US010905676B2

(12) United States Patent
Anke et al.

(10) Patent No.: US 10,905,676 B2
(45) Date of Patent: Feb. 2, 2021

(54) ANGIOTENSIN II RECEPTOR ANTAGONIST FOR THE PREVENTION OR TREATMENT OF SYSTEMIC DISEASES IN CATS

(71) Applicant: Boehringer Ingelheim Vetmedica GmbH, Ingelheim am Rhein (DE)

(72) Inventors: Sven Anke, Frankfurt am Main (DE); Stefan Johannes Lehner, Wiesbaden (DE)

(*) Notice: Subject to any disclaimer, the term of this patent is extended or adjusted under 35 U.S.C. 154(b) by 0 days.

(21) Appl. No.: 16/027,422

(22) Filed: Jul. 5, 2018

(65) Prior Publication Data

US 2019/0008831 A1    Jan. 10, 2019

Related U.S. Application Data

(60) Provisional application No. 62/529,587, filed on Jul. 7, 2017.

(51) Int. Cl.
| | | |
|---|---|---|
| *A61K 31/4178* | (2006.01) | |
| *A61K 31/4184* | (2006.01) | |
| *A61K 9/00* | (2006.01) | |
| *A61P 9/12* | (2006.01) | |

(52) U.S. Cl.
CPC ........ *A61K 31/4178* (2013.01); *A61K 9/0053* (2013.01); *A61K 31/4184* (2013.01); *A61P 9/12* (2018.01)

(58) Field of Classification Search
CPC .............. A61K 9/0053; A61K 31/4178; A61K 31/4184; A61P 9/12
See application file for complete search history.

(56) References Cited

U.S. PATENT DOCUMENTS

| 9,308,197 B2 | 4/2016 | Stark et al. |
|---|---|---|
| 9,949,964 B2 | 4/2018 | Racheboeuf |
| 2004/0110813 A1 | 6/2004 | Nakatani et al. |
| 2007/0026026 A1 | 2/2007 | Delmarre et al. |
| 2007/0155679 A1 | 7/2007 | Daemmgen et al. |
| 2008/0146543 A1 | 6/2008 | Stark et al. |
| 2012/0095069 A1 | 4/2012 | Mohr et al. |
| 2014/0288138 A1 | 9/2014 | Stark et al. |
| 2014/0364473 A1 | 12/2014 | Mohr et al. |
| 2018/0193317 A1 | 7/2018 | Stark et al. |

FOREIGN PATENT DOCUMENTS

| EP | 1579862 A1 | 9/2005 |
|---|---|---|
| EP | 1908469 A1 | 4/2008 |

OTHER PUBLICATIONS

Arenas-Lopez et al., Accuracy of enteral syringes with commonly prescribed paediatric liquid medicines. Archives of Disease in Childhood 2017, 102, 655-659. Published Feb. 24, 2017.*

Zechun Li and Qiyou Chen, "Progress in Drug Therapy for Dilated Cardiomyopathy" Chinese Medical Abstracts—Geriatrics, vol. 11, No. 1, 2002, pp. 69-72. English translation of introduction paragraph + cited paragraph Zechun Li and Qiyou Chen, "Progress in Drug Therapy for Dilated Cardiomyopathy" Chinese Medical Abstracts—Geriatrics, vol. 11, No. 1, 2002, pp. 69-72. (Chinese Language) English translation of introduction paragraph + cited paragraph provided as Non-Patent Literature Document #1 herein.

Asiedu-Gyekye et al. "Does losartan prevent cerebral edema? A preliminary study using a vascular compartment model". Medical Science Monitor, vol. 9, No. 3, Mar. 2003, pp. BR127-BR130.

Buoncompagni et al., "Treatment of Systemic Hypertension Associated With Kidney Disease." Compendium: Continuing Education for Veterinarians, Vetlearn.com, 2013, pp. E1-E6.

Champion et al., "Analysis of the Effects of Candesartan on Responses to Angiotensin II in the Hindquarters Vascular Bed of the Cat". Journal of the American Society of Nephrology, vol. 10, 1999, pp. S101-S103.

Cingolani et al., "The Positive Inotropic Effect of Angiotensin II: Role of Endothelin-1 and Reactive Oxygen Species". Hypertension, vol. 47, No. 4, Apr. 2006, pp. 727-734.

Coronel et al., "Hypertension Treatment in Nondiabetic Advanced Chronic Kidney Disease Patients with Irbesartan. Effect on Serum Uric Acid". Abstract, Journal of Hypertension, vol. 23, Supp. 2, 2005, p. S65.

Desmet et al. "Antihypertensive treatment with telmisartan in a cat with amlodipine induced gingival hyperplasia", Journal of Feline Medicine and Surgery Open Reports 1-5, 2017, pp. 1-5.

Garrison et al., "[Pro11, D-Ala12] angiotensin I has rapid onset vasoconstrictor activity in the cat". American Journal of Physiology-Endocrinology and Metabolism, vol. 273, No. 6, 1997, pp. E1059-E1064.

Glaus et al, "Efficacy of Telmisartan in Hypertensive Cats: Results of a Large European Clinical Trial", EVCIM-CA 2017 Proceedings on Aug. 28, 2017, p. 345.

Hiwada, Kunio, "Presentation of New Drug: Telmisartan". Vascular Biology & Medicine, vol. 3, No. 5, 2002, pp. 571-576.

Iino et al., "Renoprotective Effect of Losartan in Comparison to Amlodipine in Patients with Chronic Kidney Disease and Hypertension—a Report of the Japanese Losartan Therapy Intended for the Global Reneal Protection in Hypertensive Patients (JLIGHT) Study". Hypertension Research, vol. 27, No. 1, 2004, pp. 21-30.

(Continued)

*Primary Examiner* — Alicia L Otton
(74) *Attorney, Agent, or Firm* — Katrina Bergbauer

(57) ABSTRACT

A method is described for the prophylaxis or treatment of hypertension in a cat in need of such treatment. The method includes administration of a therapeutically effective amount of angiotensin II receptor 1 (AT-1) antagonist (sartan) to the cat, where the therapeutically effective amount of the sartan is administered in a daily dosage amount that is varied over a treatment period, the daily dosage amount of the sartan for a first period of time during the treatment period is 1.0 to 5.0 mg/kg of body weight, and the daily dosage amount of the sartan is decreased for a second period of time subsequent the first period of time during the treatment period.

8 Claims, 7 Drawing Sheets

(56) References Cited

OTHER PUBLICATIONS

Israili, Z.H., "Clinical pharmacokinetics of angiotensin II (AT1) receptor blockers in hypertension". Journal of Human Hypertension, vol. 14, Suppl. 1, 2000, pp. S73-S86.

Jensen et al., "Plasma renin activity and angiotensin I and aldosterone concentrations in cats with hypertension associated with chronic renal disease." American Journal of Veterinary Research, vol. 58, No. 5, May 1997, pp. 535-540.

Kumari et al., "Effect of Pre- and Posttreatment of Losartan in Feline Model of Myocardial Ischemic-Reperfusion Injury". Methods and Findings in Experimental and Clinical Pharmacology, vol. 26, No. 1, 2004, pp. 39-45.

Lazaro et al., "Forum Original Research Communication: Long-Term Blood Pressure Control Prevents Oxidative Renal Injury." Antioxidants & Redox Signaling, vol. 7, Nos. 9 & 10, 2005, pp. 1285-1293.

Mathur et al., "Evaluation of a technique of inducing hypertensive renal insufficiency in cats". American Journal of Veterinary Research, vol. 65, No. 7, Jul. 2004, pp. 1006-1013.

Mishina et al., "Non-invasive Blood Pressure Measurements in Cats: Clinical Significance of Hypertension Associated with Chronic Renal Failure." The Journal of Veterinary Medical Science, vol. 60, No. 7, 1998, pp. 805-808.

Ono et al., "Characteristics of the Long-Acting Sartan Telmisartan". Circulation Control, vol. 23, No. 4, 2002, pp. 462-466.

Semintra—Prescription Animal Remedy, Jun. 6, 2016, Retrieved From the Internet: http://files.boehringer.com.au/files/CMI/Semintra%20ANZ.pdf [retrieved on Oct. 12, 2018].

Stebbins et al., "Spinal angiotensin II influences reflex cardiovascular responses to muscle contraction". American Journal of Physiology, vol. 269, No. 4, Part 2, 1995 pp. R864-R868.

Summary of Product Information—Semintra, European Medicine Agency, Feb. 28, 2013, pp. 1-32, retrieved from the Internet: URL:https://www.ema.europa.eu/documents/product-information/semintra-epar-product-information_en.pdf [retrieved on Oct. 12, 2018].

Suzuki, Hiromichi, "Investigation of Clinical Benefits of Different Types of ARBs in Treatment of Hypertension Associated with Renal Disease." Progress in Medicine, vol. 26, No. 7, Jul. 2006, pp. 145-151 (1669-1674).

Wienen et al., "A Review on Telmisartan: A Novel, Long-Acting Angiotensin II-Receptor Antagonist". Cardiovascular Drug Reviews, vol. 18, No. 2, 2000, pp. 127-154.

Xue, Jintong. "Chapter 13. Hypertensive Disease". Practical Handbook for the Diagnosis and Treatment of Cardiovascular Disease, First Edition, Zhengzhou University Press, 2005, pp. 480-508.

\* cited by examiner

ANGIOTENSIN II RECEPTOR ANTAGONIST FOR THE PREVENTION OR TREATMENT OF SYSTEMIC DISEASES IN CATS

FIELD OF THE INVENTION

The present invention relates to the field of veterinary medicine, especially to the prophylaxis or treatment of systemic diseases in cats. In particular, the present invention relates to a method of prophylaxis or treatment of systemic diseases in cats, wherein the method comprising administration of a therapeutically effective amount of angiotensin II receptor 1 (AT-1) antagonist (sartan) to a cat in need of such a treatment.

BACKGROUND OF THE INVENTION

The prevalence of renal disease is high in aged cats, whereas chronic renal failure is considered the most important one. The prevalence of chronic kidney disease (CKD) in cats is reported to reach up to 20% with 53% of cats were older than 7 years (Lefebre, Toutain 2004, *J. Vet. Pharm. Therap.* 27, 265-281; Wolf A M North. *Am. Vet. Congress* 2006). Survival in cats with mild to moderate azotemia and extrarenal clinical signs (IRIS stage 2 & 3) ranged from 1 to 3 years. Early management and therapy is considered to successfully influence prognosis for CKD (Wolf A M North Am. Vet Congress 2006).

Chronic renal failure (CRF), at least in its final stage is, regardless of the underlying causes, characterized by irreversible structural lesions of the kidney. Thereby, progressive irreversible lesions initially localized to one portion of the nephron (e.g. glomeruli, peritubular capillaries, tubules or interstitial tissue), are eventually responsible for the development of lesions in the remaining, but initially unaffected portions of nephrons due to their functional interdependencies. New nephrons cannot be formed to replace others irreversibly destroyed by disease. In a study of biopsy findings in cats with primary renal azotemia, tubulointerstitial nephritis was observed in 70%, glomerulonephropathy occurred in 15%, lymphoma in 11% and amyloidosis was observed in 2% of the samples. CRF is recognized by reduced kidney function or the presence of kidney damage (Polzin, Osborne, Ross 2005 in: Ettinger S J, Feldman C E (eds.) *Textbook of Veterinary Internal Medicine*, $6^{th}$, Vol 2. Chapter 260, 1756 -1785).

Angiotensin II plays an important part in pathophysiology, particularly as the most potent agent for increasing blood pressure in humans. It is known that in addition to its effect of raising blood pressure Angiotensin II also has growth-promoting effects which contribute to left ventricular hypertrophy, vascular thickening, atherosclerosis, renal failure and stroke. In small animals, inhibition of the effects of Angiotensin II, via either ACE inhibitors have been shown to exhibit renoprotectiv effects through their simultaneous capacity to decrease blood pressure and control proteinuria.

Current therapy aims to delay the progression of the disease in cats by improving renal function, especially glomerular function by maintaining glomerular perfusion. This includes dietary protein restriction, modification of dietary lipid intake, phosphate restriction and treatment with angiotensin-converting enzyme (ACE) inhibitors (P. J. Barber (2004) *The Kidney, in:* Chandler E A, Gaskell C J, Gaskell R M (eds.) *Feline Medicine and Therapeutics*, 3rd edition, Blackwell Publishing, Oxford, UK).

ACE inhibitors, especially enalapril, benazepril, imidapril and ramipril, have been initially developed in small animal medicine to control chronic heart failure (CHF). Based on the pathophysiological role of the renin-angiotensin-aldosterone system (RAAS) in progression of chronic heart failure and in progression of renal damage, these agents have been shown to be useful in the treatment of chronic kidney disease (CKD) in order to delay progression of disease and reduce morbidity and suffering in small animals, including cats. Sound evidence for this is probably the recent approval of benazepril in Europe for the treatment of feline CRF (Lefebre Toutain, 2004 J Vet Pharm Therap 27, 265-281). However, the renoprotection of ACE inhibitor was likely mediated by the effect on proteinuria rather than by blood pressure reduction. This has been shown for ramipril, since the effect on blood pressure was comparable to that of placebo while the proteinuria was reduced (Remuzzi et al., 2006, *J Clin Invest* 116, (2) 288-296).

From a clinical point of view, ACE inhibitors are not the preferred target to block the RAAS because of the lack of specificity for Angiotensin I and the "angiotensin escape" phenomenon where alternate enzymatic pathways such a cathepsin, trypsin or the heart chymase can also convert Angiotensin I. Moreover, during long term treatment with ACE inhibitors, ACE activity is upregulated and Angiotensin I levels are high due the stimulated renin secretion (Burnier & Brunner, 2000, *The Lancet*, 355, 637-645).

Thus, one objective of the present invention consists in providing a new therapeutic approach for the treatment or prophylaxis of cats against chronic kidney disease.

A further more general aspect of the present invention consists in providing a new therapeutic approach for the treatment or prophylaxis of cats against systemic diseases; preferably against systemic diseases which are related to Angiotensin II or associated with the renin-angiotensin-aldosterone system (RAAS).

Still a further aspect of the present invention consists in providing a new therapeutic approach for the treatment or prophylaxis of cats against hypertension.

DETAILED DESCRIPTION OF THE INVENTION

Figure 1:
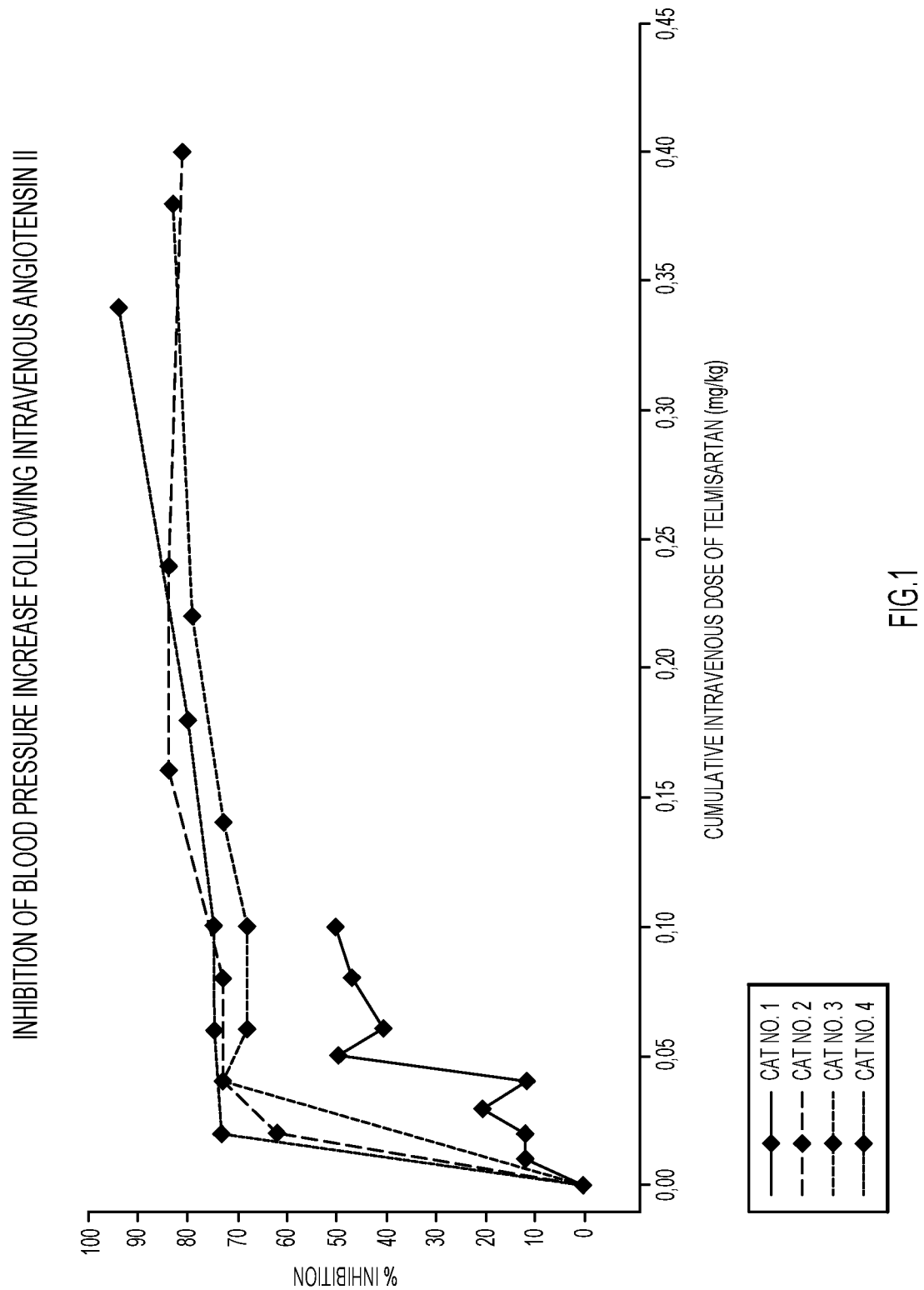
FIG. 1 is a plot of inhibition of blood pressure increase by angiotensin II receptor 1 antagonist.

Before the embodiments of the present invention it shall be noted that as used herein and in the appended claims, the singular forms "a", "an", and "the" include plural reference unless the context clearly dictates otherwise. Thus, for example, reference to "a preparation" includes a plurality of such preparations, reference to the "carrier" is a reference to one or more carriers and equivalents thereof known to those skilled in the art, and so forth. Unless defined otherwise, all technical and scientific terms used herein have the same meanings as commonly understood by one of ordinary skill in the art to which this invention belongs. All given ranges and values may vary by 1 to 5% unless indicated otherwise or known otherwise by the person skilled in the art, therefore, the term "about" was omitted from the description. Although any methods and materials similar or equivalent to those described herein can be used in the practice or testing of the present invention, the preferred methods, devices, and materials are now described. All publications mentioned herein are incorporated herein by reference for the purpose of describing and disclosing the substances, excipients, carriers, and methodologies as reported in the publications which might be used in connection with the invention. Nothing herein is to be construed as an admission that the invention is not entitled to antedate such disclosure by virtue of prior invention.

The solution to the above technical problem is achieved by the description and the embodiments characterized in the claims.

In accordance with the present invention, methods are described herein for the prophylaxis or treatment of hypertension (also referred to as high blood pressure) in a cat in need of such treatment, where the methods comprise administration of a therapeutically effective amount of angiotensin II receptor 1 (AT-1) antagonist (sartan) to the cat, the therapeutically effective amount of the sartan being administered in a daily dosage amount that is varied over a treatment period. For example, the daily dosage amount of the sartan for a first period of time during the treatment period can be 1.0 to 5.0 mg/kg of body weight, where the daily dosage amount of the sartan is decreased for a second period of time subsequent the first period of time during the treatment period.

In particular, the following items are disclosed herein:

1. An angiotensin II receptor 1 (AT-1) antagonist (sartan) for use in a method for the prophylaxis or treatment of hypertension in a cat in need of such prophylaxis or treatment, wherein the method comprises administration of a therapeutically effective amount of angiotensin II receptor 1 (AT-1) antagonist (sartan) to the cat, wherein the therapeutically effective amount of the sartan is administered in a daily dosage amount that is varied over a treatment period, the daily dosage amount of the sartan for a first period of time during the treatment period is 1.0 to 5.0 mg/kg of body weight, and the daily dosage amount of the sartan is decreased for a second period of time subsequent the first period of time during the treatment period.

2. The angiotensin II receptor 1 (AT-1) antagonist (sartan) of item 1 for use in a method for the prophylaxis or treatment of hypertension in a cat, wherein the hypertension is associated with chronic kidney disease or hyperthyroidism.

3. The angiotensin II receptor 1 (AT-1) antagonist (sartan) of item 1 for use in a method for the prophylaxis or treatment of hypertension in a cat, wherein the hypertension is idiopathic hypertension.

4. The angiotensin II receptor 1 (AT-1) antagonist (sartan) of items 1 to 3 for use in a method for the prophylaxis or treatment of hypertension in a cat, wherein the daily dosage amount is varied based upon a systolic blood pressure (SBP) value measured for the cat.

5. The angiotensin II receptor 1 (AT-1) antagonist (sartan) of items 1 to 4 for use in a method for the prophylaxis or treatment of hypertension in a cat, wherein the daily dosage amount of the sartan is decreased for the second period of time by an incremental amount ranging from 0.10 to 0.50 mg/kg of body weight.

6. The angiotensin II receptor 1 (AT-1) antagonist (sartan) of items 1 to 5 for use in a method for the prophylaxis or treatment of hypertension in a cat, wherein the daily dosage amount of the sartan is decreased when a systolic blood pressure (SBP) value measured for the cat decreases by at least 10 mmHg in relation to a baseline SBP value measured for the cat prior to the first period of time.

7. The angiotensin II receptor 1 (AT-1) antagonist (sartan) of items 1 to 6 for use in a method for the prophylaxis or treatment of hypertension in a cat, wherein the daily dosage amount of the sartan is decreased when the SBP value measured for the cat decreases by at least 20 mmHg in relation to the baseline SBP value measured for the cat determined prior to the first period of time.

8. The angiotensin II receptor 1 (AT-1) antagonist (sartan) of items 1 to 7 for use in a method for the prophylaxis or treatment of hypertension in a cat, wherein the daily dosage amount of the sartan is decreased when the SBP value measured for the cat decreases by 10 to 150 mmHg, 10 to 100 mmHg, 10 to 80 mmHg, 10 to 50 mmHg, 10 to 30 mmHg, 10 to 20 mmHg, 20 to 150 mmHg, 20 to 100 mmHg, 20 to 80 mmHg, 20 to 50 mmHg, or 20 to 30 mmHg in relation to the baseline SBP value measured for the cat determined prior to the first period of time.

9. The angiotensin II receptor 1 (AT-1) antagonist (sartan) of items 1 to 8 for use in a method for the prophylaxis or treatment of hypertension in a cat, wherein the daily dosage amount of the sartan is decreased when a systolic blood pressure (SBP) value measured for the cat decreases from a baseline SBP value measured for the cat prior to the first period of time to a value that is no greater than a threshold value.

10. The angiotensin II receptor 1 (AT-1) antagonist (sartan) of items 1 to 8 for use in a method for the prophylaxis or treatment of hypertension in a cat, wherein the daily dosage amount of the sartan is decreased when a systolic blood pressure (SBP) value measured for the cat decreases from a baseline SBP value measured for the cat prior to the first period of time to (at or below) a threshold value.

11. The angiotensin II receptor 1 (AT-1) antagonist (sartan) of item 9 or 10 for use in a method for the prophylaxis or treatment of hypertension in a cat, wherein the threshold value is no greater than 160 or 170 mmHg.

12. The angiotensin II receptor 1 (AT-1) antagonist (sartan) of item 9 or 10 for use in a method for the prophylaxis or treatment of hypertension in a cat, wherein the threshold value is 160 or 170 mmHg.

13. The angiotensin II receptor 1 (AT-1) antagonist (sartan) of items 1 to 12 for use in a method for the prophylaxis or treatment of hypertension in a cat, wherein the daily dosage amount of the sartan for the second period of time is increased or decreased for a third period of time after the second period of time and based upon a change in SBP of the cat that is measured at an end of the second period of time.

14. The angiotensin II receptor 1 (AT-1) antagonist (sartan) of items 1 to 13 for use in a method for the prophylaxis or treatment of hypertension in a cat, wherein the daily dosage amount of the sartan for a first period of time during the treatment period is 2.0 to 3.0 mg/kg of body weight, and the daily dosage amount of the sartan for the second period of time is 0.125 to 2.0 mg/kg of body weight.

15. The angiotensin II receptor 1 (AT-1) antagonist (sartan) of items 1 to 14 for use in a method for the prophylaxis or treatment of hypertension in a cat, wherein the first period of time is at least 14 days, or at least 28 days, or at least 120 days.

16. The angiotensin II receptor 1 (AT-1) antagonist (sartan) of items 1 to 15 for use in a method for the prophylaxis or treatment of hypertension in a cat, wherein the daily administration is an oral administration.

17. The angiotensin II receptor 1 (AT-1) antagonist (sartan) of items 1 to 16 for use in a method for the prophylaxis or treatment of hypertension in a cat, wherein the daily administration of the therapeutically effective amount for at least a portion of the treatment period is provided in a single dose.

18. The angiotensin II receptor 1 (AT-1) antagonist (sartan) of items 1 to 16 for use in a method for the prophylaxis or treatment of hypertension in a cat, wherein the daily administration of the therapeutically effective amount for at least a portion of the treatment period is provided in a plurality of doses.

19. The angiotensin II receptor 1 (AT-1) antagonist (sartan) of items 1 to 18 for use in a method for the prophylaxis or treatment of hypertension in a cat, wherein the method excludes administration of the therapeutically effective amount of angiotensin II receptor 1 (AT-1) antagonist (sartan) to a cat having an age that is less than 9 months.

20. The angiotensin II receptor 1 (AT-1) antagonist (sartan) of items 1 to 18 for use in a method for the prophylaxis or treatment of hypertension in a cat, wherein the angiotensin II receptor 1 (AT-1) antagonist (sartan) is administered to a cat at least 9 months of age or a cat 9 months of age and older.

21. A method for the prophylaxis or treatment of hypertension in a cat in need of such treatment, wherein the method comprises administration of a therapeutically effective amount of angiotensin II receptor 1 (AT-1) antagonist (sartan) to the cat, wherein the therapeutically effective amount of the sartan is administered in a daily dosage amount that is varied over a treatment period, the daily dosage amount of the sartan for a first period of time during the treatment period is 1.0 to 5.0 mg/kg of body weight, and the daily dosage amount of the sartan is decreased for a second period of time subsequent the first period of time during the treatment period.

22. The method of item 21, wherein the hypertension is associated with chronic kidney disease or hyperthyroidism.

23. The method of item 21, wherein the hypertension is idiopathic hypertension.

24. The method of any of items 21 to 23, wherein the daily dosage amount is varied based upon a systolic blood pressure (SBP) value measured for the cat.

25. The method of any of items 21 to 24, wherein the daily dosage amount of the sartan is decreased for the second period of time by an incremental amount ranging from 0.10 to 0.50 mg/kg of body weight.

26. The method of any of items 21 to 25, wherein the daily dosage amount of the sartan is decreased when a systolic blood pressure (SBP) value measured for the cat decreases by at least 10 mmHg in relation to a baseline SBP value measured for the cat prior to the first period of time.

27. The method of item 26, wherein the daily dosage amount of the sartan is decreased when the SBP value measured for the cat decreases by at least 20 mmHg in relation to the baseline SBP value measured for the cat determined prior to the first period of time.

28. The method of any of items 21 to 25, wherein the daily dosage amount of the sartan is decreased when a systolic blood pressure (SBP) value measured for the cat decreases from a baseline SBP value measured for the cat prior to the first period of time to a value that is no greater than a threshold value.

29. The method of item 28, wherein the threshold value is no greater than 160 or 170 mmHg.

30. The method of any of items 21 to 29, wherein the daily dosage amount of the sartan for the second period of time is increased or decreased for a third period of time after the second period of time and based upon a change in SBP of the cat that is measured at an end of the second period of time.

31. The method of any of items 31 to 30, wherein the daily dosage amount of the sartan for a first period of time during the treatment period is 2.0 to 3.0 mg/kg of body weight, and the daily dosage amount of the sartan for the second period of time is 0.125 to 2.0 mg/kg of body weight.

32. The method of any of items 21 to 31, wherein the first period of time is at least 14 days, or at least 28 days, or at least 120 days.

33. The method of any of items 21 to32, wherein the daily administration is an oral administration.

34. The method of any of items 21 to 33, wherein the daily administration of the therapeutically effective amount for at least a portion of the treatment period is provided in a single dose.

35. The method of any of items 21 to 33, wherein the daily administration of the therapeutically effective amount for at least a portion of the treatment period is provided in a plurality of doses.

36. The method of any of items 21 to 35, wherein the method excludes administration of the therapeutically effective amount of angiotensin II receptor 1 (AT-1) antagonist (sartan) to a cat having an age that is less than 9 months.

37. A kit in parts comprising:
a container containing a pharmaceutical composition in a liquid formulation comprising an angiotensin II receptor 1 (AT-1) antagonist (sartan) and one or more pharmaceutically acceptable diluents and/or carriers, the amount of sartan being within the liquid formulation in an amount that is therapeutically effective for the prophylaxis or treatment of hypertension in a cat in need of such treatment; and
a syringe comprising a barrel optionally having volumetric graduation marks optionally imprinted thereon in 0.25 mL increments or less or in 0.10 mL increments or less.

38. The kit in parts of item 37, further comprising an adaptor that connects with an open end of the container, the adaptor including an opening extending through the adaptor, wherein the adaptor opening is smaller in dimension than the container open end.

39. The kit in parts of item 37 or item 38, wherein the syringe barrel includes an open end having a geometry that corresponds with a geometry of the adaptor opening to facilitate a frictional fit between the barrel open end and the adaptor when the barrel open end is inserted into the adaptor opening.

40. The method of any of items 21 to 35 or the kit in parts of any one of items 37 to 39, wherein the cat is at least 9 months of age or is a cat 9 months of age and older.

The use of angiotensin II receptor 1 antagonists (sartans) in cats for an indication is known. Blockage of angiotensin II receptor 1 is a treatment concept which differs from blockage of angiotensin converting enzyme as known from the ACE-inhibitors. Receptor blockage is more specific and complete and further downstream in the physiologic cascade of the RAAS system. The present invention is based on certain unexpected findings, namely, that a dosage of sartan for prophylaxis or treatment of hypertension in a cat can be down titrated or decreased over a treatment period, particularly when the response in the cat is determined to be positive from such treatment (e.g., a systolic blood pressure of the cat is reduced as a result of such treatment and is further maintained at or below a certain level even with a reduction in dosage amount of the sartan being administered).

In studies, it has been found that cats tolerate a pharmacodynamically effective dose of sartans. For example, in an open-label study in nondiabetic, hypertensive human patients with proteinuric nephropathies the effects on renal outcome of low (80 mg once daily) and high dose (80 mg twice daily) telmisartan were compared. The results reinforced the concept that more effective RAAS inhibition achieved by a high dose of 160 mg daily. This dose corresponds to a plasma level of about 2800±2400 ng/ml (Cmax±SD), which exceeds the no-effect doses in toxicities studies in animals such as dogs and rats. (Investigator brochure 1994, data on file) The resulting dose of about 2 to 3 mg/kg body weight and day was thus expected to be toxic in cats. Pilot-toxicity studies have surprisingly shown that such a dose (up to 3 mg/kg) is well tolerable in cats. As used herein, the term "mg/kg" refers to dosage amount in mg per kg bodyweight of the cat.

Moreover, it was found that sartans effectively block the angiotensin II receptor 1 also in cats. This finding was unexpected, as the absolute bioavailability in cats is very low and the mean residence time and plasma half life are rather short in cats as compared to human beings. The oral bioavailability was calculated to 33.6% as compared to human beings. The mean $t_{max}$ oral was 0.44 hours and the $C_{max}$ oral was 138.1 ng/ml. The mean $t_{1/2}$ oral was 2.17 hours. The mean AUC→~oral was calculated to 150 (ng×h /m1), and the mean V/f oral was 20.41/kg. The mean AUC→~intravenous was calculated to 385 (ng×h /ml). The mean $t_{1/2}$ intravenous was 2.25 hours and the mean V/f oral was 8.8 l/kg. From this information, which was newly generated, it can be concluded that sartans, preferably telmisartan, can be used to treat cats with systemic diseases, such as chronic kidney disease, such as for example chronic renal failure, including chronic renal insufficiency.

TABLE 1

Abbreviations

| Abbreviation | Pharmacokinetic parameters |
|---|---|
| AUC | area under the plasma concentration time curve |
| C max | maximum measured plasma concentration |
| V/f | Volume of distribution (V) whereas f is the absolute bioavailability |
| MRT | mean residence time |
| t½ | terminal half-live |
| t max | time to reach Cmax |

Thus, in an embodiment, the present invention relates to a method for the prophylaxis or treatment of a systemic disease in cats, wherein the method comprises administration of a therapeutically effective amount of angiotensin II receptor 1 (AT-1) antagonist (sartan) to that cat in need of such a treatment.

The term "systemic disease", as used herein, means but is not limited to cardiovascular such as dilated cardiomyopathy (DCM), mitral valve insufficiency (MI), hypertrophic cardiomyopathy (HCM); and other acquired or hereditary heart diseases, e.g. cardiopulmonary diseases, systemic hypertension for example hypertension associated with renal diseases, chronic renal failure and other vascular diseases, or metabolic disorders such as diabetes mellitus. Thus, according to another aspect, the present invention relates to a method for the prophylaxis or treatment of a systemic disease in cats by the administration of therapeutically effective amount of said angiotensin II receptor 1 (AT-1) antagonist (sartan) to that cat, wherein the systemic disease is selected from the group of cardiovascular diseases, such as dilated cardiomyopathy (DCM), mitral valve insufficiency (MI), hypertrophic cardiomyopathy (HCM) and other acquired or hereditary heart diseases, hypertension (including systemic hypertension), metabolic disorders like diabetes mellitus.

The term "systemic hypertension", as used herein, means but is not limited to, forms of hypertension associated with renal diseases, chronic renal failure and other vascular diseases. For example, systemic hypertension can include hypertension of an unknown cause, hypertension associated with chronic kidney disease, hypertension associated with hyperthyroidism, controlled hypertension and idiopathic hypertension. In particular, systemic hypertension (also referred to herein as hypertension) is defined as a persistent elevation of the systemic blood pressure (e.g., having a Systolic Blood Pressure or SBP of 160 mmHg or greater). There are two subclassifications of hypertension: primary (or idiopathic) hypertension in which no underlying disease can be identified, and secondary hypertension occurring as a complication of a systemic disease. In recent years, idiopathic hypertension has been increasingly recognized in small animal medicine. The most common causes for secondary hypertension in cats are chronic kidney disease (CKD) and hyperthyroidism. Other diseases such as hyperaldosteronism or pheochromocytoma are very rare causes for secondary hypertension in cats and usually result in severe and often therapy resistant hypertension.

The pathogenesis of idiopathic hypertension in feline patients is not fully understood. However, activation of renin-angiotensin-aldosteron system (RAAS) is thought to be present in affected cats. Chronic kidney disease related HT is believed to be induced by the activation of RAAS and eventually aldosterone production. Effects are mainly mediated through the angiotensin-II receptor type 1 (AT-1). Chronic RAAS activation leads to persistent hypertension via systemic vasoconstriction, intravascular fluid expansion and sympathetic activation. The underlying mechanism of hypertension secondary to feline hyperthyroidism remains undetermined, although dysfunction of RAAS is suspected. In some cats, hyptertnsion is present at the time of diagnosis of hyperthyroidism, while in others hypertension develops after euthyroid state has been restored.

Regardless of the cause, hypertension can result in local or systemic disease via destructive effects to vascular beds of various organs. Clinically, hypertension related damage is frequently recognized in the eyes, brain, kidney, heart and the vessels. According to the ACVIM consensus panel on hypertension in dogs and cats (Brown et al. Guidelines for the identification, evaluation, and management of systemic hypertension in dogs and cats. ACVIM Consensus Statement. J Vet Intern Med 2007; 21: 542-558), injury to these organs resulting from persistent elevation of systolic blood pressure (SBP) is collectively termed target organ damage (TOD), where TOD refers to a continuum of reversible to irreversible injury and relatively mild to potentially life-threatening consequences. Hypertension in cats possesses a significant risk for further organ damage. Activation and/or dysfunction of RAAS appears to play a crucial role in the development of feline hypertension of various causes. Consequently, RAAS inhibition seems a reasonable therapeutic target for hypertensive cats with either idiopathic hypertension, or secondary hypertension due to CKD or hyperthyroidism.

Thus, in another embodiment, the present invention relates to a method for the prophylaxis or treatment of systemic hypertension (also referred to herein as hypertension) in cats, where the method comprises administration of a therapeutically effective amount of angiotensin II receptor 1 (AT-1) antagonist (sartan) to a cat in need of such a treatment, where the hypertension is associated with one or more other systemic diseases including (without limitation) CKD, hyperthyroidism, controlled hypertension and idiopathic hypertension. In a further embodiment, the therapeutically effective amount of the sartan is administered to a cat in a daily dosage amount that is varied over a treatment period. The variation of the treatment period can be a daily dosage amount of the sartan for a first period of time during the treatment period that is 1.0 to 5.0 mg/kg of body weight, and the daily dosage amount of the sartan is decreased for a second period of time subsequent the first period of time during the treatment period. The daily dosage amount of the sartan can be decreased for the second period of time by an incremental amount ranging from 0.10 to 0.50 mg/kg of body weight. In an embodiment, the daily dosage amount of the sartan can be decreased for the second period of time by an incremental amount ranging from 0.10 to 0.50 mg/kg of the cat's body weight. The daily dosage amount of the sartan can be decreased based upon a certain criteria for the cat, such as a measured systolic blood pressure (SBP) of the cat. For example, the daily dosage amount of the sartan can be decreased when a SBP value measured for the cat decreases by at least 10 mmHg in relation to a baseline SBP value measured for the cat prior to the first period of time. In another embodiment, the daily dosage amount of the sartan can be decreased when a SBP value measured for the cat is no greater than a predetermined or threshold value (e.g., 120 mmHg). As described herein, a daily dosage amount of sartan can be further decreased in any suitable amounts for any number of consecutive dosage periods and based upon a positive response by the cat to such decreased dosage.

In humans, angiotensin II receptor 1 (AT1 receptor antagonists (sartans) are known to significantly reduce proteinuria in both diabetic and non-diabetic patients, even in those with mild to moderate chronic renal failure (CRF). Moreover, there is published evidence for the efficacious use of AT1 receptor antagonists for treatment of nephropathies in type II diabetes Cupisti A, et al., 2003, *Biomed Pharmacother*; 57 (3-4): 169-172; Rysava R, et al., 2005, *Press Monit*; (10(4): 207-213; WO92/10182). In cats tubulointerstitial nephritis is reported to be the major causative (>70%) finding for CRF whereas in human beings and dogs glomerulonephropathy is more prominent compared to cats. Glomerular lesions are more often seen in dogs and humans and consequently the clinical finding of moderate to marked proteinuria, resulting from loss of glomerular permselectivity, is more common in dogs and humans. Tubulointerstitial nephritis as seen in cats showed less proteinuria. Proteinuria is recognized as an important predictor of disease progression in humans and dogs with spontaneous kidney disease and reduction of proteinuria is associated with improved outcome in clinical trials to show the renoprotective effects of blocking the RAAS by either ACE or ARBs in human suffering from nephropathy (Karalliede & Viberti, *J. Human Hypertension* 2006). Due to the fact that there is less proteinuria in cats because of the tubulointerstitial origin of CRF, the reduction of proteinuria as renoprotective effect in delaying progression of CRF might be expected to be less important in this species. However, in a clinical field trial an independent and significant correlation between proteinuria (determined as UPC) and survival in cats suffering from CRF have been reported. Surprisingly, even in azotemic cats with only minor proteinuria (acc. to IRIS, UPC <0.25) this correlation was evident (Syme, Elliot 2006, *J Vet Intern Med*, 20, 528-535).

Thus, according to a preferred embodiment the systemic disease is chronic kidney disease, preferably chronic renal failure, e.g. as defined as stage II to IV in Table 2.

The diagnosis of reduced kidney function such as chronic renal failure is based upon exclusion of pre- and postrenal causes and standard blood markers, e.g. urea and creatinine in plasma or serum. Abnormal concentrations of these parameters are described as azotemia. Standard urine markers of reduced kidney function include urine specific gravity, proteinuria and others (Polzin D J, Osborne C A, Ross S, 2005: *Chronic Kidney Disease, In:* Ettinger S J, Feldman E C (ed.) *Textbook of Veterinary Internal Medicine 6th edition*, W. B. Saunders Company, Philadelphia, USA). The international renal interest society (IRIS) has proposed a staging system based on azotemia to define CRF patients (Polzin D J 2006: *Treating feline kidney disease: an evidence-based approach, Proceedings of The North American Veterinary Conference*). The main category for staging being plasma creatinine [mg/dl], which is completed by two subcategories independent from stage, urine protein:creatinine ratio (UPC) and blood pressure [mmHg]. With the applied system, feline patients are staged along a continuum of progressive kidney disease.

TABLE 2

Stages of feline chronic kidney disease

| Stage | Plasma creatinine (mg/dl) | Comments | Subcategory UPC (independent from stage) | Subcategory systolic blood pressure (mmHg, independent from stage) |
|---|---|---|---|---|
| I | <1.6 | Non-azotemic: some other renal abnormality is present | <0.2 = Non-proteinuric 0.2-0.4 = Borderline proteinuric >0.4 = Proteinuric | <150 = minimal risk of end-organ damage 150-159 = low risk of end-organ damage 160-179 = moderate risk of end-organ damage ≥180 = high risk of end-organ damage |
| II | 1.6-2.8 | Mildly azotemic: usually mild clinical signs | | |
| III | 2.9-5.0 | Moderately azotemic: many extra-renal clinical signs | | |

TABLE 2-continued

Stages of feline chronic kidney disease

| Stage | Plasma creatinine (mg/dl) | Comments | Subcategory UPC (independent from stage) | Subcategory systolic blood pressure (mmHg, independent from stage) |
|---|---|---|---|---|
| IV | >5.0 | Severly azotemic: invasive life support methods required | | |

As described herein, a method for the prophylaxis or treatment of chronic renal failure in cats comprises administration of a therapeutically effective amount of angiotensin II receptor 1 (AT-1) antagonist (sartan) to that cat in need of such a treatment and wherein said chronic renal failure is characterized by any one of the clinical manifestations as listed in table 2, or any combination thereof. For example, the present invention relates to a method for the prophylaxis or treatment of cats having an plasma creatine of ≥1.6 (mg/dl of blood), and/or having a proteinuric of ≥0.2 (subcategory UPC), wherein the method comprises administration of a therapeutically effective amount of angiotensin II receptor 1 (AT-1) antagonist (sartan) to that cat in need of such a treatment.

A comprehensive list of angiotensin II receptor antagonists can be found on pages 2 to 22 of WO 92/10182 and pages 7 to 18 of WO 95/26188, which all are incorporated herein by reference. Angiotensin II receptor antagonists are described inter alia in EP-A-253310, EP-A-323841, EP-A-324377, EP-A-420237, EP-A-443983, EP-A-459136, EP-A-475206, EP-A-502314, EP-A-504888, EP-A-514198, WO 91/14679, WO 93/20816, WO 02/092081, U.S. Pat. No. 4,355,040, U.S. Pat. No. 4,880,804 and U.S. Pat. No. 6,028,091. Forms which are frequently mentioned are sartans, such as candesartan, eprosartan, irbesartan, losartan, olmesartan, tasosartan, telmisartan or valsartan. Those which are particularly preferred according to the present invention are irbesartan, losartan and telmisartan. All of these sartans, or pharmaceutical salts or polymorphs thereof are well known to a person skilled in the art, and its use is within the meaning of the present invention.

Thus the present invention relates to a method for the prophylaxis or treatment of cats suffering from a systemic disease, preferably from chronic kidney disease, e.g. chronic renal failure, wherein the method comprising administration of a therapeutically effective amount of angiotensin II receptor 1 (AT-1) antagonist (sartan) to that cat in need of such a treatment and wherein the angiotensin II receptor 1 (AT-1) antagonist (sartan) is selected from the group consisting of: candesartan, eprosartan, irbesartan, losartan, olmesartan, tasosartan, telmisartan or valsartan, preferably of irbesartan, losartan and telmisartan.

Telmisartan is an angiotensin II receptor antagonist developed for the treatment of hypertension and other medical indications as disclosed in EP-A-502314. Its chemical name is 4'-[2-n-propyl-4-methyl-6-(1-methylbenzimidazol-2-yl)-benzimidazol-1-ylmethyl]-biphenyl-2-carboxylic acid having the following structure:

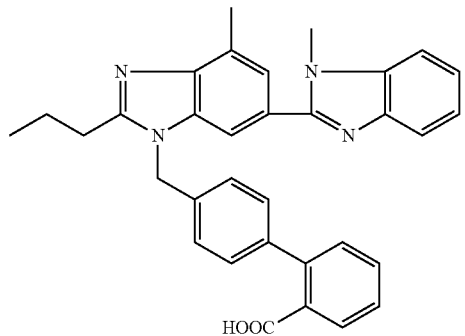 [SMILES: CCCc1nc2c(C)cc(-c3nc4ccccc4n3C)cc2n1Cc1ccc(-c2ccccc2C(=O)O)cc1]

Telmisartan is already sold on the market under the trade name Micardis® (Boehringer Ingelheim, Germany) for treatment/prophylaxis of humans. Telmisartan is also licensed in the EU under the trade name Semintra® for the reduction of proteinuria associated with CKD in cats. It exists in two polymorphic forms as disclosed in WO 00/43370, U.S. Pat. No. 6,358,986 and U.S. Pat. No. 6,410,742. Sodium salts of telmisartan and its solvate, hydrate, and hemihydrate are disclosed in WO 03/037876.

Thus, according to a further embodiment, the present invention relates to a method for the prophylaxis or treatment of a systemic disease in cats, such as chronic kidney disease, e.g. chronic renal failure, wherein the method comprising administration of a therapeutically effective amount of telmisartan or pharmaceutically acceptable salt thereof, preferably of a telmisartan as mentioned above.

As already mentioned herein, it has been surprisingly found that use of telmisartan effectively inhibits the angiotensin II receptor pressure response in cats. Moreover, it has been found that doses of less than 0.05 mg telmisartan per kg body weight of cat led to an inhibition of the blood pressure response of about 75% in the majority of the tested cats. Moreover, a study in laboratory cats was established to investigate the Angiotensin II induced increase in diastolic blood pressure prior to and after administration of telmisartan. This test was established to estimate the potency as well as the duration of action of sartans, in particular of telmisartan in cats. Approximately 24 hours after the last oral dosing, diastolic blood pressure responses to increasing intravenous doses of Angiotensin II were significantly reduced when the target dose of telmisartan was compared with Placebo. Thus it could be concluded that administration of the target dose, despite the short elimination half-life and bioavailability, in the cat given once daily is capable to exhibit the intended pharmacodynamic action and duration.

Thus, according to another aspect, the present invention relates to a method for the prophylaxis or treatment of a systemic disease in cats, preferably of chronic kidney disease, e.g. chronic renal failure, wherein the method comprising administration of a therapeutically effective amount of angiotensin II receptor 1 (AT-1) antagonist (sartan), preferably telmisartan or pharmaceutically acceptable salt thereof, to that cat in need of such a treatment, wherein the therapeutically effective amount of such angiotensin II receptor 1 (AT-1) antagonist is about 0.01 to about 10 mg/kg of body weight. Preferably, said therapeutically effective amount of such angiotensin II receptor 1 (AT-1) antagonist is about 0.05 to about 8 mg/kg of body weight, even more preferably about 0.1 to about 5 mg/kg of body weight, even more preferably about 0.2 to about 4 mg/kg of body weight, even more preferably about 0.3 to about 3 mg/kg of body weight, even more preferably about 0.4 to about 2.5 mg/kg of body weight, even more preferably about 0.5 to about 2 mg/kg of body weight, most preferred about 0.75 to about 1.5 mg/kg of body weight. Thus, said therapeutically effective amount of such angiotensin II receptor 1 (AT-1) antagonist is for example 0.01, 0.02, 0.03, . . . 0.08, 0.09, 0.1, etc.; 0.11, 0.12, 0.125, 0.13, . . . 0.18, 0.19, 0.2, etc.; 0.21, 0.22, 0.23, . . . 0.28, 0.29, 0.3 etc. . . . ; 0.81, 0.82, 0.83, . . . 0.88, 0.89, 0.9 etc.; 0.91, 0.92, 0.93, . . . 0.98, 0.99, 1.0 etc.; 1.01, 1.02, 1.03, . . . 1.08, 1.09, 1.1 etc.; . . . 1.2, 1.3, . . . 1.8, 1.9, 2.0 etc.; 2.1, 2.2, 2.3, . . . 2.8, 2.9, 3.0 etc.; . . . ; 8.1, 8.2, 8.3, . . . 8.8, 8.9, 9.0 etc.; 9.1, 9.2, 9.3, . . . 9.8, 9.9, 10 mg/kg of body weight. Angiotensin II receptor 1 (AT-1) antagonist, preferably telmisartan may be administered once, twice or thrice a day in a daily dosage as mentioned above.

In cases when angiotensin II receptor 1 (AT-1) antagonist is administered by parenteral route, said angiotensin II receptor 1 (AT-1) antagonist, preferably telmisartan is administered in a dosage of about 0.01 to about 4 mg/kg of body weight. Preferably, said therapeutically effective amount of such angiotensin II receptor 1 (AT-1) antagonist is about 0.05 to about 3 mg/kg of body weight, even more preferably about 0.1 to about 2.5 mg/kg of body weight, even more preferably about 0.15 to about 2.0 mg/kg of body weight, even more preferably about 0.2 to about 1.5 mg/kg of body weight, most preferred about 0.25 to about 1.25 mg/kg of body weight. Thus, said therapeutically effective amount of such angiotensin II receptor 1 (AT-1) antagonist is for example 0.01, 0.02, 0.03, . . . 0.08, 0.09, 0.1, etc.; 0.11, 0.12, 0.13, . . . 0.18, 0.19, 0.2, etc.; 0.21, 0.22, 0.23, . . . 0.28, 0.29, 0.3 etc. . . . ; 0.81, 0.82, 0.83, . . . 0.88, 0.89, 0.9 etc.; 0.91, 0.92, 0.93, . . . 0.98, 0.99, 1.0 etc.; 1.01, 1.02, 1.03, . . . 1.08, 1.09, 1.1 etc.; . . . 1.1, 1.2, 1.3, . . . 1.8, 1.9, 2.0 etc.; 2.1, 2.2, 2.3, . . . 2.8, 2.9, 3.0 etc.; 3.1, 3.2, 3.3, . . . 3.8, 3.9, 4 mg/kg of body weight. Angiotensin II receptor 1 (AT-1) antagonist, preferably telmisartan may be administered once twice or trice a day in a daily dosage as mentioned above.

In cases when angiotensin II receptor 1 (AT-1) antagonist, preferably telmisartan is administered by oral, rectal, nasal or inhalative route a dosage of about 0.03 to about 10 mg/kg of body weight is preferred. Preferably, said therapeutically effective amount of such angiotensin II receptor 1 (AT-1) antagonist is about 0.10 to about 8 mg/kg of body weight, even more preferably about 0.20 to about 7.5 mg/kg of body weight, even more preferably about 0.25 to about 7.0 mg/kg of body weight, even more preferably about 0.25 to about 6.0 mg/kg of body weight, most preferred about 0.25 to about 5 mg/kg of body weight. Thus, said therapeutically effective amount of such angiotensin II receptor 1 (AT-1) antagonist is for example 0.03, 0.04, 0.05, . . . 0.08, 0.09, 0.1, etc.; 0.11, 0.12, 0.13, . . . 0.18, 0.19, 0.2, etc.; 0.21, 0.22, 0.23, . . . 0.28, 0.29, 0.3 etc. . . . ; 0.81, 0.82, 0.83, . . . 0.88, 0.89, 0.9 etc.; 0.91, 0.92, 0.93, . . . 0.98, 0.99, 1.0 etc.; 1.01, 1.02, 1.03, . . . 1.08, 1.09, 1.1 etc.; . . . 1.1, 1.2, 1.3, . . . 1.8, 1.9, 2.0 etc.; 2.1, 2.2, 2.3, . . . 2.8, 2.9, 3.0 etc.; . . . ; 8.1, 8.2, 8.3, . . . 8.8, 8.9, 9.0 etc.; 9.1, 9.2, 9.3, . . . 9.8, 9.9, 10 mg/kg of body weight. Telmisartan may be administered once twice or trice a day in a daily dosage as mentioned above.

According to another aspect of the invention, the present invention relates to a method for the prophylaxis or treatment of a systemic disease in cats, such as chronic kidney disease, e.g. chronic renal failure, wherein the method comprising administration of a therapeutically effective amount of angiotensin II receptor 1 (AT-1) antagonist (sartan), preferably telmisartan or pharmaceutically acceptable salt thereof, to that cat in need of such a treatment, wherein the therapeutically effective amount of such angiotensin II receptor 1 (AT-1) antagonist is administered in a therapeutically effective amount that result in an cumulative intravenous concentration of at least 0.025 mg/kg of body weight (bw) Preferably, said angiotensin II receptor 1 (AT-1) antagonist (sartan), preferably telmisartan is administered to an cumulative intravenous concentration of at least 0.05 mg/kg of bw, more preferably of 0.1 mg/kg of bw, even more preferably 0.15 mg/kg of bw even more preferably 0.2 mg/kg of bw, even more preferably 0.25 mg/kg of bw, even more preferably 0.40 mg/kg of bw, even more preferably 0.5 mg/kg of bw, even more preferably 0.75 mg/kg of bw, even more preferably 1 mg/kg of bw. Upper limits of cumulative intravenous concentration of about 1 mg/kg of bw are well tolerable, however, cumulative intravenous concentrations of up to 5, 4, 3 and 2 mg/kg of bw are also within the meaning of the present invention as well as any further higher non-toxic cumulative intravenous concentration of said angiotensin II receptor 1 (AT-1) antagonist (sartan). A person skilled in the art, in view of the teaching given herein, is entitled to estimate that upper non-toxic cumulative intravenous concentration by standard techniques.

Optionally, the angiotensin II receptor 1 (AT-1) antagonist (sartan), preferably telmisartan can be administered in combination with other drugs. Such other drugs are, for example Ca-channel blockers (e.g. Amlodipine), beta-blockers (e.g. Atenolol, Carvediol), cardiotonic-Ca-sensitising agents (e.g. Pimobendan, Levosimendan), selective If-current inhibitors (i.e. Cilobradine, Ivabradine), ACE inhibitors (e.g. ramipril, benazepril, enalapril); anti-obesity drugs (such as Amphetamine derivatives, Sibutramine, Orlistat, Rimonabat) and the like. Thus, according to another aspect, the present invention relates to a method for the prophylaxis or treatment of a systemic disease in cats, preferably of chronic kidney disease, e.g. chronic renal failure, wherein the method comprising administration of a therapeutically effective amount of angiotensin II receptor 1 (AT-1) antagonist (sartan), preferably telmisartan or pharmaceutically acceptable salt thereof, together with another active substance, to that cat in need of such a treatment, wherein said further active substance is a Ca-channel blocker (e.g. Amlodipine), beta-blocker (e.g. Atenolol, Carvediol), cardiotonic-Ca-sensitising agent (e.g. Pimobendan, Levosimendan), selective If-current inhibitor (i.e. Cilobradine, Ivabradine), ACE inhibitor (e.g. ramipril, benazepril, enalapril); an anti-obesity drug (such as Amphetamine derivatives, Sibutramine, Orlistat, Rimonabat) and the like.

Telmisartan and the other active compounds can be orally administered in a wide variety of different dosage forms, i.e., they may be formulated with various pharmaceutically acceptable inert carriers in the form of tablets, capsules, lozenges, troches, hard candies, powders, sprays, aqueous suspensions, elixirs, syrups, and the like. Such carriers include solid diluents or fillers, sterile aqueous media and various non-toxic organic solvents. Moreover, such oral pharmaceutical formulations can be suitably sweetened and/ or flavored by means of various agents of the type commonly employed for such purposes. In general, the compounds of this invention are present in such oral dosage forms at concentration levels ranging from about 0.5% to about 90% by weight of the total composition, in amounts which are sufficient to provide the desired unit dosages. Other suitable dosage forms for the compounds of this invention include controlled release formulations and devices well known to those who practice in the art.

For purposes of oral administration, tablets containing various excipients such as sodium citrate, calcium carbonate and calcium phosphate may be employed along with various disintegrants such as starch and preferably potato or tapioca starch, alginic acid and certain complex silicate, together with binding agents such as polyvinylpyrrolidone, sucrose, gelatin and acacia. Additionally, lubricating agents such as magnesium stearate, sodium lauryl sulfate and talc or compositions of a similar type may also be employed as fillers in soft and hard-filled gelatin capsules; included lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying agents and/or water, ethanol, propylene glycol, glycerin and various like combinations thereof.

For purposes of parenteral administration, solutions of the compounds in sesame or peanut oil or in aqueous propylene glycol may be employed, as well as sterile aqueous solutions of the corresponding pharmaceutically acceptable salts. Such aqueous solutions should be suitably buffered if necessary, and the liquid diluent rendered isotonic with sufficient saline or glucose. These particular aqueous solutions are especially suitable for intravenous, intramuscular and subcutaneous injection purposes. In this connection, the sterile aqueous media employed are readily obtained by standard techniques well known to those skilled in the art. For instance, distilled water is ordinarily used as the liquid diluent and the final preparation is passed through a suitable bacterial filter such as a sintered glass filter or a diatomaceous earth or unglazed porcelain filter. Preferred filters of this type include the Berkefeld, the Chamberland and the Asbestos Disk-Metal Seitz filter, wherein the fluid is sucked into a sterile container with the aid of a suction pump. The necessary steps should be taken throughout the preparation of these inject-able solutions to insure that the final products are obtained in a sterile condition.

For purposes of transdermal administration, the dosage form of the particular compound or compounds may include, by way of example, solutions, lotions, ointments, creams, gels, suppositories, rate-limiting sustained release formulations and devices therefore. Such dosage forms comprise the particular compound or compounds and may include ethanol, water, penetration enhancer and inert carriers such as gel-producing materials, mineral oil, emulsifying agents, benzyl alcohol and the like.

These preformulated combinations of active substances are generally incorporated with one or more formulation adjuvants such as mannitol, sorbitol, xylitol, saccharose, calcium carbonate, calcium phosphate, lactose, croscarmellose sodium salt (cellulose carboxymethylether sodium salt, cross-linked), crospovidone, sodium starch glycolate, hydroxypropylcellulose (low-substituted), maize starch, polyvinylpyrrolidone, copolymers of vinylpyrrolidone with other vinyl derivatives (copovidone), hydroxypropylcellulose, hydroxypropylmethylcellulose, microcrystalline cellulose or starch, magnesium stearate, sodium stearylfumarate, talc, hydroxypropylmethylcellulose, carboxymethylcellulose, cellulose acetate phthalate, polyvinyl acetate, water, water/ethanol, water/glycerol, water/sorbitol, water/polyethyleneglycol, propyleneglycol, cetylstearyl alcohol, carboxymethylcellulose or fatty substances such as hard fat or suitable mixtures thereof, into conventional galenic preparations such as plain or coated tablets, capsules, powders, suspensions or suppositories.

Tablets may be obtained for example by mixing the active substance or substances with one or more excipients and subsequently compressing them. The tablets may also consist of several layers. Examples of excipients are:
  inert diluents such as mannitol, sorbitol, xylitol, saccharose, calcium carbonate, calcium phosphate and lactose;
  disintegrants such as croscarmellose sodium salt (cellulose carboxymethylether sodium salt, cross-linked), crospovidone, sodium starch glycolate, hydroxypropylcellulose (low-substituted) and maize starch;
  binders such as polyvinylpyrrolidone, copolymers of vinylpyrrolidone with other vinyl derivatives (copovidone), hydroxypropylcellulose, hydroxypropylmethylcellulose, microcrystalline cellulose or starch;
  lubricants such as magnesium stearate, sodium stearyl fumarate and talc;
  agents for achieving delayed release such as hydroxypropylmethylcellulose, carboxymethylcellulose, cellulose acetate phthalate and polyvinyl acetate; and
  pharmaceutically permitted colourings such as coloured iron oxides.

Furthermore, if telmisartan is used in combination with another drug used for the prophylaxis or treatment of a systemic disease, preferably of chronic kidney disease, e.g. chronic renal failure in cats, the pharmaceutical composition according to the invention may be a kit of parts which comprises:
  a first containment containing a pharmaceutical composition comprising a therapeutically effective amount of telmisartan or a physiologically acceptable salt thereof and one or more pharmaceutically acceptable diluents and/or carriers; and
  a second containment containing another drug used for the prophylaxis or treatment of a systemic disease, preferably chronic renal failure, or a physiologically acceptable salt thereof and one or more pharmaceutically acceptable diluents and/or carriers.

A preferred kit of parts comprises one or more Ca-channel blockers (e.g. Amlodipine), beta-blockers (e.g. Atenolol, Carvediol), cardiotonic-Ca-sensitising agents (e.g. Pimobendan, Levosimendan), selective If-current inhibitors (i.e. Cilobradine, Ivabradine), ACE inhibitors (e.g. ramipril, benazepril, enalapril); anti-obesity drugs (such as Amphetamine derivatives, Sibutramine, Orlistat, Rimonabat) and the like, in the second containment.

According to a further aspect, the present invention also relates to the use of an angiotensin II receptor 1 (AT-1) antagonist (sartan), preferably of telmisartan for the manufacture of a pharmaceutical composition comprising a therapeutically effective amount of said angiotensin II receptor 1 (AT-1) antagonist for the treatment of a systemic disease in cats.

Preferably the systemic disease is selected from the group of cardiovascular diseases, such as dilated cardiomyopathy (DCM), mitral valve insufficiency (MI), hypertrophic cardiomyopathy (HCM) and other acquired or hereditary heart diseases, systemic hypertension, for example hypertension associated with renal diseases, chronic kidney disease (CKD) and other vascular diseases, metabolic disorders like diabetes mellitus. For example, the systemic disease is systemic hypertension associated with one or more of CKD, hyperthyroidism, controlled hypertension and idiopathic hypertension.

Preferred sartans are those mentioned in an exemplarily manner supra. Most preferred is the use of telmisartan or any pharmaceutically acceptable salt thereof, such as Micardis® or Semintra®. The preferred doses which can be used according to the invention are those mentioned supra. Preferred administration routes are orally, bucally, parenterally, nasally, rectally or topically, whereas the oral administration being most preferred. Parenteral administration may include subcutaneous, intravenous, intramuscular and intrasternal injections and infusion techniques.

In another embodiment of the invention, administration of a dosage of a sartan (e.g., telmisartan) is regulated during treatment of a cat and based upon a condition associated with the cat. The dosage regulation can be modified after certain treatment periods and in dependence upon a measured change (e.g., improvement) in a physical condition of a cat. For example, in treatment of a cat for hypertension (e.g., hypertension associated with one or more of CKD, hyperthyroidism, controlled hypertension and idiopathic hypertension), a sartan can be administered to the cat at an initial dosage amount (e.g., any of the suitable dosage amounts as previously described herein) and then modified after a certain time period, where the modification in dosage amount can be based upon the measured systolic blood pressure (SBP) of the cat. The SBP of the cat can be measured in any suitable manner (e.g., utilizing a blood pressure cuff wrapped around the tail or a limb of the cat). In example embodiments (e.g., such as certain examples described herein), an initial daily dosage amount can be administered to a cat for a certain time period, where the SBP of the cat is determined after such time period. In the event the determined SBP of the cat is not greater than a threshold value, the daily dosage amount can be reduced or titrated down to a smaller amount. Further reductions or down titrations of the daily dosage amount can be implemented in the dosage regimen in the event the SBP of the cat remains below the threshold value and/or drops even further below the threshold value. Alternatively, in other embodiments, the daily dosage amount can also be increased or titrated up in the event the SBP determined for a cat is at a value that exceeds the threshold value by a predetermined amount. The dosages can be administered in any suitable manner such as those previously described herein (e.g., orally, parenterally, etc.) and can further be in any suitable form (e.g., solid or liquid) and combined with any other suitable active ingredient or any other excipient or other substance as previously noted herein.

According to a further aspect of the present invention the present invention relates to an angiotensin II receptor 1 (AT-1) antagonist (sartan), preferably telmisartan or a pharmaceutically acceptable salt thereof, for the use in a method of treating hypertension in a cat, wherein the therapeutically effective amount of the sartan is administered in a daily dosage amount that is varied over a treatment period, the daily dosage amount of the sartan for a first period of time during the treatment period is 1.0 to 5.0 mg/kg of body weight, and the daily dosage amount of the sartan is decreased for a second period of time subsequent the first period of time during the treatment period. In a specific embodiment said hypertension is hypertension which is associated with chronic kidney disease or hyperthyroidism or said hypertension is idiopathic hypertension.

In example embodiment, an initial dosage amount of a sartan can be administered to a cat for treatment of hypertension in an amount of from about 0.10 to about 8.0 mg/kg, such as about 0.10 to about 5.0 mg/kg, about 0.75 to about 5.0 mg/kg, or about 1.0 to 3.0 mg/kg (e.g., about 1.5 mg/kg or about 2.0 mg/kg), where such dosage amount can be administered once per day, twice per day or three times (thrice) per day. For example, a daily dosage amount of the sartan to be administered to the cat can be from about 0.10 to about 8.0 mg/kg, such as from about 1.0 to about 4.0 mg/kg, from about 2.0 to about 3.0 mg/kg, etc. A decrease or down titration in daily dosage (as well as an increase or up titration in daily dosage) between a first predetermined or prescribed time period and a second (subsequent) prescribed time period can be in any suitable amount, e.g., a change in daily dosage or incremental change (i.e., an incremental increase or decrease or, in other words, an increase or decrease by a predetermined or stepped amount) in a range of about 0.05 to about 1.0 mg/kg, or about 0.1 to about 0.5 mg/kg, etc. For example, changes in daily dosage titration between a first prescribed time period and a second (subsequent) prescribed time period can be modified or adjusted by a delta or incremental (decreased or increased) change of about 1.0 mg/kg, about 0.9 mg/kg, about 0.8 mg/kg, about 0.75 mg/kg, about 0.5 mg/kg, about 0.4 mg/kg, about 0.3 mg/kg, about 0.25 mg/kg, about 0.2 mg/kg, about 0.125 mg/kg, about 0.1 mg/kg, by 0.05 mg/kg or in any other suitable incremental amount (i.e., any other set decreased or set increased amount).

The daily dosage amount of a sartan administered to a cat can be adjusted over any selected number of time intervals. For example, the initial time period (e.g., a time period including day one of treatment) for the initial daily dosage amount of the sartan administered to a cat for treatment of hypertension can be from about 1 day to about 30 days or more, such as from about 5 days to about 28 days, from about 7 days to about 14 days, etc. At the end of the initial time period, an adjustment that is made in the daily dosage amount can be implemented for a second or subsequent time period that can be from about 1 day to about 30 days or more, such as from about 5 days to about 28 days, from about 7 days to about 14 days, etc. Any further number of subsequent time periods of adjustment in daily dosage can be further implemented as desired and based upon efficacy of treatment. In some embodiments, the total treatment period at which a cat can be treated with varying daily dosage amounts (e.g., over certain periods of time) can be at least about 120 days (e.g., a treatment period can last for at least 3 months, at least 4 months, at least 5 months, at least 6 months, etc.).

The methods for treatment or prophylaxis of hypertension in cats by administration of a sartan (including modification of dosage of the sartan during a treatment period) have been determined to be effective for cats varying in ages. However, no study has been conducted to determine the effectiveness of such methods for a cat having an age of less than 9 months. Accordingly, the treatment methods described herein are preferably for cats having an age of at least 9 months (i.e., an age of 9 months and older). Further, the treatment methods described herein exclude cats having an age of less than 9 months.

As noted herein, for the treatment or prophylaxis of hypertension for a cat by administration of a sartan to the cat, the SBP of the cat can be used as the criteria for determining whether an adjustment in the daily dosage to the cat can be implemented. In example embodiments, it may be desirable to adjust the daily dosage of the sartan administered to the cat when the SBP of the cat drops below (for down titration or decreased dosage) a first threshold value or rises above (for up titration or increased dosage) a second threshold value. For example, in a scenario in which, after the initial treatment period, the SBP of the cat decreases below or is no greater than a first threshold value, the daily dosage amount for administration to the cat can be reduced by any amount (e.g., any of the dosage incremental values as noted herein). An example threshold SBP value can be set, e.g., within a range from about 120 mmHg to about 170 mmHg. For example, a threshold SBP value can be set at no greater than about 170 mmHg, no greater than about 165 mmHg, no greater than about 160 mmHg, no greater than about 155 mmHg, no greater than about 150 mmHg, no greater than about 145 mmHg, no greater than about 140 mmHg, no greater than about 135 mmHg, no greater than about 130 mmHg, no greater than about 125 mmHg, no greater than about 120 mmHg or any values there between.

Alternatively, or in combination with establishing a threshold SBP value, a change in SBP value or delta SBP value (where the change or delta is the difference between two SBP values) for the cat can also trigger a modification in the daily dosage amount administered the cat. For example, a change in SBP value that will trigger a change in dosage amount administered to the cat can be from about 10 mmHg to about 150 mmHg, about 10 mmHg to about 100 mmHg, about 10 mmHg to about 80 mmHg, about 10 mmHg to about 50 mmHg, about 10 mmHg to about 30 mmHg, about 10 mmHg to about 20 mmHg, about 20 mmHg to about 150 mmHg, about 20 mmHg to about 100 mmHg, about 20 mmHg to about 80 mmHg, about 20 mmHg to about 50 mmHg, about 20 mmHg to about 30 mmHg, or about 5 mmHg to about 30 mmHg, such as from about 10 mmHg to about 25 mmHg, with further examples being a change in SBP value of at least about 5 mmHg, at least about 10 mmHg, at least about 15 mmHg, at least about 20 mmHg, at least about 25 mmHg, or at least about 30 mmHg.

In preferred embodiments, the methods of regulation (change in dosage amount) are implemented by administration of the sartan to a cat as a liquid formulation (e.g., any suitable liquid formulation of the types previously described herein). In such embodiments, a suitable dispenser can be provided to facilitate administration at varying dosage amounts. However, the methods of regulation can also be implemented by administration of the sartan as a solid formulation (e.g., as a tablet).

For liquid formulations, a kit of parts can be provided which includes a containment containing a liquid formulation of a pharmaceutical composition comprising a therapeutically effective amount of telmisartan or a physiologically acceptable salt thereof and one or more pharmaceutically acceptable diluents and/or carriers, and a suitable dispenser for dispensing dosages to a cat in varying amounts in accordance with a dosage regimen as described herein. In other words, a suitable dispenser is provided to facilitate a change in dosage amount (e.g., a decrease/down titration or an increase/up titration in dosage) based upon a change in physical condition (e.g., change in SBP) of the cat during the course of treatment.

A suitable dispenser for the liquid formulation comprises a syringe including printed indicia or graduation marks on the barrel of the syringe defining any suitable number of volumetric increments for the liquid formulation to be drawn within the syringe barrel for administration to the cat. In an example embodiment, the syringe has a size ranging from 1.0 mL to 6.0 mL or greater (e.g., from 2.0 mL to 5.0 mL) and further includes graduation marks in 0.05 mL increments, in 0.1 mL increments, in 0.25 mL increments, in 0.50 mL increments, and/or in any other suitable graduations or increments. By providing a liquid formulation having a suitable concentration of the sartan within solution, such volumetric increments of the syringe are suitable for enabling administration of the sartan to a cat in the varying dosage amounts (e.g., from 0.1 to 8.0 mg/kg) based upon the weight of the cat.

Some non-limiting examples of down titration dosage schemes (which are also described in greater detail in Examples 4-6 below) are as follows.

A. A sartan (e.g., telmisartan) is administered in liquid form (e.g., using a 10 mg/mL telmisartan solution, and a 2 mL dosing syringe demarcated in 0.10 mL or smaller increments) to a cat for the treatment or prophylaxis of hypertension at a daily dosage amount of 3.0 mg/kg (e.g., in two doses per day, each dosage amount being 1.5 mg/kg) for an initial period of 14 days. The daily dosage amount is modified based upon SBP measurements of the cat, e.g., at periodic veterinary visits (e.g., every 2-4 weeks). The cat can have hypertension associated with chronic kidney disease (CKD), hypertension associated with hyperthyroidism, controlled hypertension and/or idiopathic hypertension. Initially (e.g., at or before a first veterinary visit at Day 0), a baseline SBP of the cat is measured. After the initial 14 day period of treatment (e.g., at a second veterinary visit, such as at Day 14 of the treatment period), the daily dosage amount is decreased or down titrated to 2.0 mg/kg (e.g., in one dose per day). The daily dosage can be further decreased depending upon the SBP value measured for the cat (e.g., at a third visit, such as at Day 28 of the treatment period). For example, a decrease in SBP from the baseline SBP value (obtained for the cat prior to the initial period of administration of the sartan) of at least 20 mmHg can result in a decrease in daily dosage. Alternatively (or in combination with a measured decrease in SBP from baseline SBP), a decrease in SBP to a value no greater than a threshold value (where the threshold value is, e.g., 120 mmHg) can result in a decrease in daily dosage. The daily dosage can be decreased by about 1.0 mg/kg or less (e.g., about 0.5 mg/kg, about 0.4 mg/kg, about 0.3 mg/kg, about 0.25 mg/kg, about 0.2 mg/kg, about 0.15 mg/kg, about 0.125 mg/kg, about 0.1 mg/kg or about 0.05 mg/kg). Periodically, the dosage can be further decreased in the same or different incremental amounts (e.g., at the second visit, third visit, etc. of the treatment period) based upon the cat either maintaining the SBP value at no greater than the threshold value and/or maintaining a decrease in SBP of at least about 20 mmHg over a sufficient time period (e.g., 14 days or less). In this example, the initial daily dosage is 3.0 mg/kg, and such daily dosage can be decreased or titrated down (based upon sufficient decrease in SBP) to a daily dosage value ranging from 0.125 mg/kg to 2.0 mg/kg. For example, the daily dosage can be titrated down from 3.0 mg/kg 4 2.0 mg/kg 4 1.0 mg/kg 4 0.5 mg/kg, etc., where such down titration is implemented when the SBP value of the cat after a certain time period (e.g., 14 days or less) is maintained at no greater than a threshold value (e.g., no greater than 120 mmHg) and/or is maintained at a value lower than at least about 20 mmHg from the baseline SBP value for the cat. In a specific example embodiment, the daily dosage amount for the cat can be set at 2.0 mg/kg (e.g., single daily dosage) when the SBP for the cat is maintained within 120-180 mmHg, and is further down titrated (e.g., to 1.5 mg/kg 4 1.0 mg/kg 4 0.5 mg/kg) when the SBP for the cat is maintained at no greater than 120 mmHg. The treatment period for the cat can be, e.g., 26 weeks (i.e., 6 months)

with visits every 2-4 weeks to determine whether an adjustment is to be made in daily dosage of the sartan based upon the SBP value measured for the cat (e.g., where the daily dosage can be down titrated based upon the SBP value for the cat being maintained at no greater than 120 mmHg).

B. A sartan (e.g., telmisartan) is administered in liquid form (e.g., using a 4 mg/mL telmisartan solution, and a 5 mL dosing syringe demarcated in 0.25 mL or smaller increments) to a cat for the treatment or prophylaxis of hypertension at a daily dosage amount of 2.0 mg/kg (e.g., in one dose per day) for an initial period of 28 days. The daily dosage amount is modified based upon SBP measurements of the cat, e.g., at periodic veterinary visits (e.g., every 2-4 weeks). The cat can have hypertension associated with chronic kidney disease (CKD), hypertension associated with hyperthyroidism, controlled hypertension and/or idiopathic hypertension. After the initial period, the daily dosage is decreased or down titrated if the cat has a SBP no greater than 160 mmHg. The down titration of the daily dosage can be in increments of 1.0 mg/kg or less (e.g., about 0.5 mg/kg, about 0.4 mg/kg, about 0.3 mg/kg, about 0.25 mg/kg, about 0.2 mg/kg, about 0.15 mg/kg, about 0.125 mg/kg, about 0.1 mg/kg or about 0.05 mg/kg). For example, the initial daily dosage of 2.0 mg/kg can be decreased or down titrated to 1.5 mg/kg if the SBP of the cat is no greater than 160 mmHg. Further subsequent decreases or down titrations in daily dosage (e.g., 1.5 mg/kg 1.0 mg/kg 0.5 mg/kg) can also be implemented in the treatment regimen when the SBP of the cat is maintained at no greater than 160 mmHg for a sufficient time period (e.g., from 2-4 weeks) between visits (e.g., between a current visit and the previous visit) and at the current daily dosage. In this example, the initial daily dosage is 2.0 mg/kg, and such daily dosage can be decreased or titrated down (based upon sufficient decrease in SBP) to a daily dosage value ranging from 0.125 mg/kg to 2.0 mg/kg (e.g., from 0.5 mg/kg to 2.0 mg/kg) when the SBP value for the cat is no greater than a threshold value (e.g., SBP no greater than 160 mmHg).

In certain scenarios, the dosage can be increased or up titrated after having been decreased or down titrated in a previous portion of the treatment period if the SBP of the cat has increased to an undesirable value or by an undesirable amount. For example, consider a scenario in which the daily dosage amount of a sartan to a cat was decreased from 3.0 mg/kg daily to 1 mg/kg daily (due to a decrease in SBP to no greater than 120 mmHg and/or a decrease from baseline SBP of at least 20 mmHg). In a subsequent time period (e.g., within 14 days of the down titration in dosage), if the SBP of the cat has increased significantly (e.g., the current SBP is 120 mmHg or greater or the current SBP is no longer at least 20 mmHg less than the baseline SBP), the daily dosage of sartan for the cat can be increased or up titrated to a greater value (e.g., the original amount, or to 3.0 mg/kg or to 2.0 mg/kg). During the next period at which the SBP of the cat is measured, an optional further adjustment (decrease or increase) in daily dosage can be implemented depending upon the response of the cat to the change in dosage (based upon the currently measured SBP vs. the previously measured SBP and/or the baseline SBP).

Figure 6A:
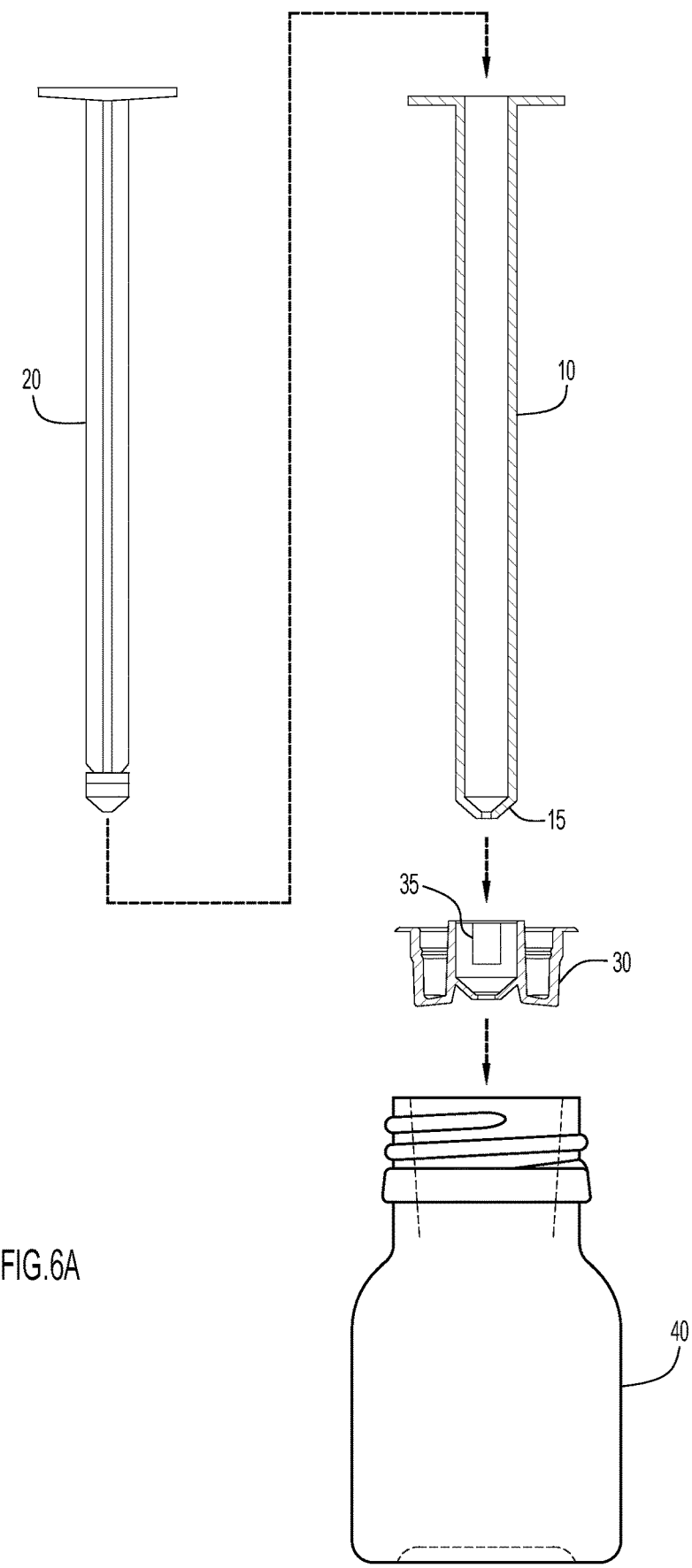
FIGS. 6A and 6B depict an example embodiment of a medicament containing and administration system for a kit in parts for use with the methods described herein, where the system includes a plunger and a container to store medicament.
Figure 6B:
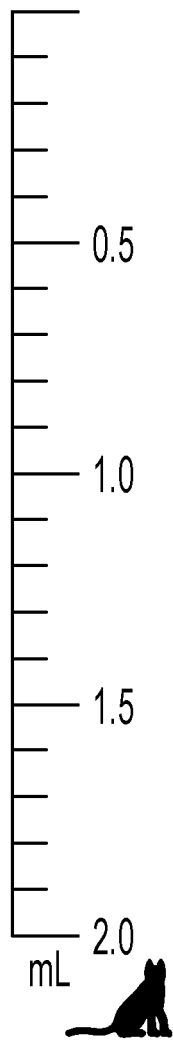

As previously noted, a kit of parts can be provided which includes a containment system for a liquid formulation of a pharmaceutical composition comprising a therapeutically effective amount of sartan (e.g., telmisartan or a physiologically acceptable salt thereof) and one or more pharmaceutically acceptable diluents and/or carriers, and a suitable dispenser for dispensing dosages to a cat in varying amounts in accordance with a dosage regimen (e.g., down titrating, up titrating, etc.) as described by the embodiments herein. An example embodiment of a kit of parts is depicted in FIGS. 6A and 6B. Referring to FIG. 6A, the kit of parts includes a syringe comprising a barrel 10 and a plunger 20 configured to fit and frictionally move or slide in a telescoping manner within the barrel 10 (to facilitate aspiration of the plunger to draw fluid into the barrel and forcing fluid flow from the barrel via the plunger), a vial or container 40, and a plug-in adaptor 30 configured to facilitate withdrawal of fluid into the barrel 10 from the open end of the container 40 during use. The syringe and container components can be constructed of any suitable materials acceptable to ensure effective operation of the components to deliver the desired dosage amount of the sartan to a cat being treated. For example, the barrel 10 can be constructed of polypropylene material, the plunger 20 can be constructed of a high density polyethylene material, the plug-in adaptor 30 can be constructed of a low density polyethylene material, and the container 40 can be constructed of a high density polyethylene material. In addition, the syringe and container components can have any suitable dimensions and geometric configurations that facilitate suitable interactivity with each other and suitable operational performance during administration of the sartan solution to a cat being treated. In an example embodiment, the container 40 has a volumetric capacity of at least about 45 mL and contains a 10 mg/mL telmisartan solution. The container 40 further includes a cap (not shown) to close the open end of the container during periods of non-use.

The syringe and container components can further have any dimensions (length, width, inner diameter, outer diameter, etc.) suitable for their intended purposes. As an example, the barrel 10 can have a length dimension of 87 mm-89 mm, an outer diameter of 8.0 mm-8.6 mm and an inner diameter of 6.6 mm-6.8 mm, where such dimensions enable the barrel to hold at least 2.0 mL of solution. The plunger 20 and other container components can also have suitable dimensions that facilitate suitable engagement and/or interaction with the syringe barrel.

The syringe barrel 10 includes an open end 15 through which the solution is aspirated (via the plunger 20) from the container 40. The barrel open end 15 has a frustoconical shape that corresponds in geometrical shape and dimension(s) with a corresponding central opening 35 of the adaptor 30, where the adaptor central opening 35 extends through the adaptor (e.g., along a central axis of the adaptor). In particular, the interior wall surfaces defining the adaptor central opening 35 correspond in dimension(s) and shape such that, when the barrel open end 15 is inserted within the adaptor central opening 35, the barrel open end frictionally and snugly fits within the adaptor central opening. The frictional engagement between the barrel open end 15 and the interior wall surfaces of the adaptor central opening 35 can further provide a fluid tight seal between the engaging surface portions between barrel 10 and adaptor 30 such that fluid is only transferred from the container 40, through the adaptor central opening 35, and into the barrel 10 via its open end 15. Referring to FIG. 6B, the barrel 10 further includes demarcations on its exterior surface that facilitate aspiration of a precise amount of the sartan solution from the container 40 into the barrel in 0.1 mL increments. In particular, the demarcations are in 0.1 mL increments from 0 to 2.0 mL. Such incremental demarcations, combined with the amount of sartan in solution within the container 40, facilitate administration of dosages of sartan to a cat in any suitable amounts as described herein (including down titrating and up titrating in any suitable amounts as described herein).

The plug-in adaptor 30 also has a suitable external diameter or transverse cross-section that corresponds with the opening in the container 40 so as to provide a snug, friction and fluid tight fit with the container. The adaptor central opening 35 is smaller in cross-sectional dimension or diameter than the cross-sectional dimension or diameter of the container open end. Thus, when the adaptor 30 is inserted in a plug fit arrangement and secured into the opening of the container 40 (with the adaptor opening 35 facing upward or away from the container opening), the adaptor 30 reduces the dimension(s) of the opening or fluid passage from the container 40 that facilitates withdrawal of sartan solution from the container.

The corresponding geometries and dimensions of the barrel open end 15 and adaptor central opening 35 further serve as a "key" that ensures that only the syringe barrel 10 (with demarcations as set forth in FIG. 6B) can be effectively used with the adaptor 30. In other words, any other syringe barrel having a different shaped and/or different dimensioned open end will not fit securely within the adaptor central opening 35 to facilitate adequate aspiration of fluid from the container 40. At the same time, the syringe barrel 10 is only suitable for use with the adaptor 30 provided with the kit in parts. This therefore ensures that the barrel 10 (with its demarcations) cannot be exchanged with another kit in parts that may include a different adaptor and/or container that includes a different type of medicament (e.g., a kit in parts that includes a container having a different medicament or a sartan solution having a different mg/mL amount of sartan within the solution).

EXAMPLES

The following examples serve to further illustrate the present invention; but the same should not be construed as a limitation of the scope of the invention disclosed herein.

Example 1

The aim of this exploratory study was to investigate the pharmacokinetic behaviour in plasma and the absolute bioavailability of telmisartan in male and female cats following a single oral or intravenous administration.

Four clinically healthy male and female domestic short hair cats (HsdCpb: CADS) with a body weight range of 2.6-4.2 kg were used in this study. The animals were randomly allocated to 2 groups, 2 animals per group. The study was designed as a 2×2 cross-over trial (i.e. two periods, days 1 and 15) in which the test article telmisartan was given by single oral or intravenous administration at a dose of 1 mg/kg body weight.

Blood samples were drawn at 0 h (i.e. prior to treatment), 5 (after i. v. injection only), 15, 30 and 60 min as well as 2, 4, 8, 24, 72 and 96 h after each treatment. Clinical observations were also conducted at these time points. Plasma samples were sent to the analytical laboratory and analysed there using a validated method. The plasma levels measured in each animal were subjected to various pharmacokinetic calculations.

The results of this study may be summarised as follows:

No specific clinical signs were noted during the entire course of the study.

Pharmacokinetic analyses for telmisartan revealed the following results:

TABLE 3

| | Route of Administration | | |
|---|---|---|---|
| Parameter | | oral | i.v. |
| t max [hour] | mean | 0.438 | — |
| C max [ng/ml] | mean | 138.10 | — |
| AUC 0 → ∞ [ng · h/ml] | mean | 150.426 | 384.751 |
| AUC 0 → ∞ [ng · h/ml] | mean | 138.598 | 375.945 |
| t½ [hour] | mean | 2.169 | 2.252 |
| Cl/f or Cl [ml/min · kg] | mean | 171.588 | 45.535 |
| V/f or V [l/kg] | mean | 20.453 | 8.856 |
| MRT [hour] | mean | 1.969 | 0.789 |

The points estimate for the absolute bioavailability were 0.316 for AUC 0→t and 0.336 for AUC 0→∞ with respective 95% confidence intervals of 0.086-1.165 and 0.0,90-1.245. Individual data showed that the bioavailability was clearly lower in animal no. 101 (i.e. 0.116 for AUC 0→∞) in comparison with the other animals (i.e. 0.387-0.582).

The test article telmisartan was well tolerated after a single oral or intravenous administration to cats at a dose of 1 mg/kg body weight.

Mean plasma concentrations increased until 15-30 min after oral administration of telmisartan and declined rapidly afterwards. No quantifiable plasma concentrations could be found at 24 h after both routes, orally and intravenously.

The absolute bioavailability after oral administration was found to be 33%.

Example 2

The aim of this study was to investigate the effects of an escalating intravenous dose of telmisartan on the blood pressure response of anaesthetised cats after administration of angiotensin II. The originally intended endpoint of the study was to find a dose of telmisartan which inhibits ≥90% of the angiotensin blood pressure response.

Four clinically healthy adult male and female domestic short hair cats (HsdCpb: CADS) with a body weight range of 2.5-3.5 kg were used in this study. The animals were anaesthetised with sodium pentobarbital and anaesthesia was sustained by continuous infusion of diluted anaesthetic. A catheter was inserted into a carotid artery and connected to a pressure transducer for registration of the arterial pressure. Another catheter was placed into the femoral vein for administration of angiotensin II (A2) or the test article telmisartan. The systolic and diastolic blood pressure [mmHg] in the carotid artery were recorded and analysed at discrete intervals as described below.

At first, the diastolic blood pressure was registered 6 times every 5 minutes. The mean of these 6 measurements were set as the baseline blood pressure. Then two bolus injections of A2 were administered at a dose of 0.1 μg/kg in an interval of 10 min. The maximum increase in diastolic blood pressure obtained from the second A2-bolus relative to the baseline blood pressure was taken as the control angiotensin II-blood pressure response (i.e. reference value).

Five minutes after the reference value was obtained, the first injection of telmisartan was administered. Thirty minutes later the diastolic blood pressure was recorded, immediately followed by bolus injection of A2 at a dose of 0.1 μg/kg and the maximum increase in diastolic blood pressure was obtained. This procedure was to be repeated accordingly until the intended endpoint of the experiment (i.e. an A2-pressure response ≤10% of the control A2-pressure response corresponding to ≥90% inhibition) was reached. During the course of the experiment it had been shown that the dose of telmisartan had to be increased at single time points in order to increase the effect. In addition, the endpoint of a 90% inhibition could not be reached in 3 of 4 animals even after several consecutive steps as described above so that the experiment was terminated in these individual animals before. At the end of the experiment, the anaesthetised animals were euthanized with an overdose of sodium pentobarbital.

The results of this study may be summarised as follows (see FIG. 1):

The mean baseline diastolic blood pressure of the individual animals ranged from 82-99 mmHg and the control angiotensin II-blood pressure response was between 34 and 63 mmHg.

After treatment with telmisartan, the response pattern was similar in 3 animals (i.e. animal nos. 102, 151, 152). In these animals the maximal inhibition of the blood pressure increase relative to the control angiotensin II-blood pressure response was roughly 80-95% in contrast to 50% inhibition in animal no. 101.

However, the final cumulative dose of the test article was only 0.1 mg/kg in this animal whereas this dose ranged between 0.34 and 0.4 mg/kg in the other animals.

In animal no. 101 the maximum effect of 50% inhibition was reached at a cumulative dose of 0.05 mg/kg. In animal nos. 102 and 152 a 73% inhibition was already reached after the 1st dose of 0.04 and 0.02 mg/kg, respectively. In animal no. 151 the same inhibition of 73% was reached at a cumulative dose of 0.04 mg/kg. In all 4 animals, further escalation of the dose did not produce markedly higher effects which were appropriately related to the increase of the dose.

In conclusion, escalating intravenous doses of the test article telmisartan led to an inhibition of the diastolic blood pressure increase in anaesthetised cats after administration of angiotensin II.

An inhibition of 73% was found at the cumulative dose of 0.04 mg/kg telmisartan in 3 of 4 animals. In one animal, a maximum inhibition of 50% was observed at a cumulative dose of 0.05 mg/kg. In all 4 animals, further dose escalations did not produce an appropriate dose response relationship.

Example 3

The aim of this blinded controlled, randomised exploratory study was to investigate the safety of telmisartan in male and female cats after repeated oral administration over four weeks.

Twelve clinically healthy approximately 1 year old male and female, domestic short hair cats (HsdCpb: CADS) with a body weight range of 2. 5-5. 1 kg were used in this study. The animals were allocated to 3 groups, 4 animals per group. All animals were treated with the test article telmisartan or control article (i.e. placebo) once daily on days 0 to 27. The test/control article was administered orally at three different does levels of 0.0 (placebo; group I), 1 (group II) and 3 (group III) mg telmisartan/kg body weight. The bottles with the test/control article looked identical with the exception of the animal no. in order to achieve blinding.

Blood samples for haematology and clinical chemistry were collected from the animals on days-1 (i.e. prior to the first treatment) and again on days 3, 7, 14, 28. Body weights were measured weekly and electrocardiography recording were made on days −1, 14, 21 and 28. A detailed physical examination including determination of rectal temperature and respiratory rate was carried out on days -1, 7, 14, 22 and 28. Systolic blood pressure (once daily) and heart rate (twice daily) were determined five days per week beginning prior to treatment until necropsy. The palatability of the administered article was assessed at various time points throughout treatment using a scoring system. On day 28 of the study, all animals were subjected to necropsy and stomach and kidneys were examined histopathologically. Relevant parameters were analysed using appropriate statistical procedures.

The results of this study can be summarised as follows:

No clinical findings clearly attributable to the treatment with the test article were observed during the entire study period.

Although no significant differences were found the results of the assessment of the palatability might indicate a slightly impaired palatability of the test article formulation. However, the palatability was predominantly good or acceptable in the animals of both treated groups II and III.

Physical and ECG examinations did not reveal treatment-related findings at all time points of investigation.

No significant differences were found in the body weights, rectal temperature, respiratory and heart rates during the course of the study.

The systolic blood pressure was significantly lower in the treated groups II and III compared to the control group I on single occasions after initiation of treatment. In addition, differences of borderline significance were found including the time before treatment. Changes from baseline did not reveal significant differences between treated groups and controls. However, the course of the mean values over time might suggest a tendency of a slight reduction of the systolic blood pressure in groups II and III compared to group I from day 20 onwards.

No treatment-related differences were found between treated groups and the concurrent controls in the haematological and clinical chemistry parameters including the differential leukocyte count on each day of examination during the study. Urinalysis did also not provide evidence of a treatment effect.

No animal showed any specific finding during necropsy.

Histopathology revealed a few findings in stomach and kidneys but there were no histopathological findings considered to be associated with the treatment.

Due to the exploratory nature of this study the number of animals per treatment group was rather low. Taking this fact into consideration the results of the present study may permit the following conclusions:

A slightly impaired palatability of the test article formulation containing telmisartan might be identified.

The course of the mean values over time might suggest a tendency of a slight reduction of the systolic blood pressure in the animals treated with telmisartan towards the end of the study period.

The test article telmisartan was well tolerated after repeated oral administration over 4 weeks to cats at doses of 1 and 3 mg/kg body weight.

Example 4

A U.S. study was conducted to evaluate the safety and effectiveness of telmisartan in cats with systemic hypertension, where the primary variable for statistical analysis was mean Systolic Blood Pressure (mSBP) reduction from baseline (Day 0) to Visit 2 (Day 14 ±2) and Visit 3 (Day 28 ±2).

The change in mSBP from baseline to Visit 3 was deemed clinically significant if a reduction in mSBP was at least 20 mmHg.

Domestic cats, one year of age or older, that met the enrollment criteria defined in the protocol were randomly assigned to treatment with telmisartan oral solution (Investigational Veterinary Product, IVP) or placebo (Investigational Control Product, ICP) in a 2:1 randomization scheme. Of a total of 9,157 cases screened (representing 7,605 individual cats), 290 cases met the criteria for enrollment. The most common reason for screen failure (90% of cases) was that the cat did not have hypertension. Two of the 290 cases enrolled were excluded from the safety and efficacy populations as they were immediately removed from the study and did not receive any IVP or ICP. Of the remaining 288 cats used for the safety summary, 192 received IVP and 96 received ICP from a total of 33 sites within the United States (US) and Canada. From this population, an additional 67 cats were excluded, leaving a total of 221 cats from 20 sites to be included in the efficacy analysis, representing 142 IVP-treated and 79 ICP-treated cats. Overall, both treatment groups were evenly distributed with regard to demographics and baseline characteristics including age, body weight, mSBP, retinal/fundic changes, and laboratory values. The median age of cats enrolled in this study was 14.2 years.

Cats were classified as belonging to one or more of three subpopulations of hypertension: CKD and/or hyperthyroidism and idiopathic hypertension. A specific breakdown of the cats in the study classified in the subpopulations is set forth in Table 4:

TABLE 4

Number of cats in each subpopulation

| Subpopulation | Placebo | Telmisartan | Total (N) |
|---|---|---|---|
| CKD | 42 | 82 | 124 (56.1%) |
| Idiopathic | 27 | 39 | 66 (29.9%) |
| CKD and Hyperthyroid | 9 | 16 | 25 (11.3%) |
| Hyperthyroid | 1 | 5 | 6 (2.7%) |
| Total Across Subpopulations | 79 | 142 | 221 |

A cat could have been enrolled into the CKD and hyperthyroid populations if it had both diseases. The majority of the cats in the safety and efficacy populations (-68%) were enrolled into the CKD subpopulation. The idiopathic hypertension subpopulation represented approximately 29% of the enrolled cats, followed by the hyperthyroid subpopulation at approximately 14%. The percentages do not total 100% because a majority of the hyperthyroid subpopulation cats were also represented in the CKD subpopulation. When this group is separated into an additional subpopulation (CKD and hyperthyroid), it represents approximately 11% of the safety and the efficacy populations.

The two treatment groups (IVP and ICP) were similarly balanced with regard to the baseline mSBP (determined at Visit 1). The minimum and maximum mSBP were identical for both treatment groups. Overall, the two treatment groups were comparable in the pretreatment mSBP values, as set forth in Table 5:

TABLE 5

Mean SBP values at baseline

| Baseline mSBP for cats in efficacy analysis | Placebo (mmHg) | Telmisartan (mmHg) |
|---|---|---|
| Mean | 175 | 177 |
| Median | 175 | 176 |
| Minimum | 160 | 160 |
| Maximum | 200 | 200 |

Upon enrollment into the study, cats were orally administered telmisartan by their owners, where the owners were given the option of dosing the treatments around or on the food or via syringe. A dosing syringe was provided with demarcations in 0.1 mL increments as well as a dose and volume to be given, rounded to the nearest 0.1 mL (where the calculation was based on kg of body weight for each cat at Visit 1, and the dose was recalculated at each subsequent visit using the current body weight).

The cats were started on a 1.5 mg/kg twice daily (BID) dose (i.e., 3 mg/kg daily dosage) of either IVP or ICP for reduction of mSBP. Following Visit 2 (approximately Day 14), the dose was decreased to the 2 mg/kg once daily (SID) maintenance dose. The reduction and maintenance dosage regimen for the cats in the study is set forth in Table 6:

TABLE 6

Treatment Groups

| Treatment type | Minimum number of cats | Phase | Time Period (days) | Dose of active ingredient (rate) | Dosage (volume) |
|---|---|---|---|---|---|
| Telmisartan Oral Solution (IVP) | ≥160 | Reduction | Days 1-14 (±2) | 1.5 mg/kg BID | 0.375 mL/kg BID |
|  |  | Maintenance | Days 15-28 (±2) | 2 mg/kg SID | 0.5 mL/kg SID |
| Negative Control (ICP) | ≥80 | Reduction | Days 1-14 (±2) | 0 mg/kg BID | 0.375 mL/kg BID |
|  |  | Maintenance | Days 15-28 (±2) | 0 mg/kg SID | 0.5 mL/kg SID |

The maintenance dose for a cat in the study could be further down-titrated if the mSBP of the cat remained below 120 mmHg from Visit 2 (at about day 14) and onward. For cats having such reduced mSBP, the dose was reduced by decreasing the current dosage by 50% (e.g., dosage reduced from 2 mg/kg SID to 1 mg/kg SID, and then from 1 mg/kg SID to 0.5 mg/kg SID). The down titration dosage regimen for cats maintaining a mSBP below 120 mmHg is set forth in Table 7:

TABLE 7

Maintenance dosing

| Treatment type | mSBP observed (mmHg) | Treatment Dosage of active ingredient (rate) | Product dose (volume) |
|---|---|---|---|
| Telmisartan Oral Solution (IVP) | >180 | Rescue | Rescue |
| | 180-120 | Maintenance: 2 mg/kg SID | Maintenance: 0.5 mL/kg SID |
| | <120 | Down Titration: 1 mg/kg SID** | Down Titration: 0.25 mL/kg SID** |
| Negative Control (ICP) | >180 | Rescue | Rescue |
| | 180-120 | 0 mg/kg | 0.5 mL/kg SID |
| | <120 | 0 mg/kg | 0.25 mL/kg SID** |

**After a cat received 1 mg/kg SID dosing, additional dose reduction was allowed to a minimum of 0.5 mg/kg SID or 0.125 mL/kg SID if mSBP was <120 mmHg.

Only 14 cats in the safety population had doses down-titrated during the study, whereas the majority of cats were maintained on the 2 mg/kg SID maintenance dose following Visit 2.

Baseline physical examination parameters, including mSBP and retinal photographs, were obtained and compared to Visit 2 and Visit 3 (approximately Day 28) to assess possible hypertension-related Target Organ Damage (TOD). Baseline blood and urine values were obtained and compared to Visit 3 to determine the clinical significance of changes in laboratory values. At Visit 2 and at Unscheduled Visits, blood and urine samples were collected at the discretion of the Investigator. Changes in all parameters were summarized by treatment group as well as by subpopulation, if appropriate.

The primary variable for statistical analysis was mSBP reduction from baseline observed at Visit 2. In addition, the arithmetic mean reduction at Visit 3 in the telmisartan group must have been ≥20 mmHg to demonstrate clinical relevance. Telmisartan was successful in fulfilling both primary criteria for efficacy in cats as described below.

The change in mSBP from baseline (Visit 1) to Visit 2 was calculated for each cat, and the mean change from baseline for each treatment group was determined as set forth in Table 8:

TABLE 8

Change in mSBP

| Treatment Group | N | LSM mSBP change from baseline to Visit 2 (ΔmmHg)* | Lower 95% CI (ΔmmHg)** | Upper 95% CI (ΔmmHg)** | p-value comparison to placebo |
|---|---|---|---|---|---|
| Placebo | 79 | −7.5 | −13.6 | −1.5 | • |
| Telmisartan | 141+ | −23.3 | −28.2 | −18.3 | 0.0005 |

+One cat had a valid Visit 3 but not a valid Visit 2 and thus was removed from the Visit 2 means calculation.
*LSM: Least Squares Means
**CI = Confidence Interval There was a statistically significant difference (p=0.0005) between the telmisartan and placebo groups. The telmisartan group had a mean decrease of mSBP of 23.3 mmHg, while the placebo group had a mean decrease in mSBP of 7.5 mmHg. A placebo effect was seen in the study; however, it was not considered to be a clinically relevant decrease in mSBP. Therefore, telmisartan was successful in statistically significantly reducing mSBP when compared to placebo. Further, a clinically relevant reduction in mSBP was pre-defined to be ≥>20 mmHg in the telmisartan group at Visit 3 (at about Day 28), where the means of the treatment group at baseline (Visit 1) minus the means of the treatment group at Visit 3 were calculated. A resultant arithmetic mean decrease of 23.9 mmHg for the IVP group was determined. These results of the efficacy analysis of this study confirm telmisartan is effective for the reduction and control of hypertension in cats.

With regard to the efficacy of the down titration (decrease in daily dosage) for cats maintaining a mSBP of lower than 120 mmHg, the data in Table 9 shows the down titration of telmisartan to certain cats in the study:

TABLE 9

Cases down-titrated at each visit by new dose and treatment group

| Visit | | IVP Cases | | ICP Cases | Total |
|---|---|---|---|---|---|
| | | 1 mg/kg/day | | | |
| Visit 2 | n = 11 | 358-406, 329-535, 329-454, 323-533, 323-416, 322-631, 322-460, 308-754, 303-423, 265-836, 263-567 | n = 3 | 330-408, 325-528, 318-512 | 14 |
| Unscheduled | n = 0 | None* | n = 1 | 325-430 | 1 |
| Visit 3 | n = 8 | 330-509, 330-404, 325-560, 318-597, 317-405, 308-591, 308-474, 298-556 | n = 0 | None | 8 |
| | | 0.5 mg/kg/day | | | |
| Visit 2 | n = 0 | None | n = 0 | None | 0 |
| Unscheduled | n = 1 | 323-416 | n = 0 | None | 1 |
| Visit 3 | n = 2 | 329-454, 358-406 | n = 0 | None | 2 |

*Case 305-402 is not included in this table because the dose was titrated at an Unscheduled Visit while the cat was in acute renal failure and the Owner was instructed to stop all medications At Visit 2, 14 cats (11 telmisartan and three placebo) were assigned a lower dose (1.0 mg/kg SID) due to having a mSBP <120 mmHg. Ten of the 11 telmisartan cats were enrolled in an extended-use study at Visit 3 (see Example 5). Three of the 10 telmisartan cats (329-454, 323-416, and 358-406) continued to have a mSBP <120 mmHg following Visit 2 and were further decreased in dose to 0.5 mg/kg SID. The remaining 7 of the 10 telmisartan cats remained on the 1.0 mg/kg dose through the end of the study. The eleventh telmisartan cat (263-567) was assigned a lower dose at Visit 2; however, the cat was actually removed from the study at that visit due to experiencing a serious adverse event (SAE). At Visit 3, 8 telmisartan cats were assigned a lower dose of 1.0 mg/kg SID and two telmisartan cats were assigned a lower dose of 0.5 mg/kg SID due to having a mSBP <120 mmHg. All 10 cats were subsequently enrolled into the extended-use study (Example 5).

In this study, the incidence of target organ damage (TOD) was similar in the IVP and placebo groups and was low overall. When evaluating retinal lesions, the majority of the photos scored the "same"; but there was a slight numerical increase in the percentage of IVP cats (11.5%) compared to ICP cats (8.1%) scoring "better", and roughly no difference in the percentage of cats with retinal lesions scoring "worse" between the two treatment groups. Thus, this study suggests that telmisartan does not cause retinal deterioration and may promote improvement by decreasing the deleterious effects of hypertension on the retina. This study further confirms the safety of telmisartan in this population of hypertensive cats. There were very few Serious Adverse Events (SAEs) attributable to telmisartan. The most common AEs (vomiting, diarrhea, lethargy, and weight loss) are common findings in geriatric cat studies, especially when cats are given oral medication. Vomiting, diarrhea, and lethargy occurred slightly more often in the IVP group in comparison to the ICP group.

In conclusion, the data from this study demonstrates the safety and efficacy of telmisartan oral solution to control hypertension in cats under clinical conditions at doses of 1.5 mg/kg BID (i.e., 3.0 mg/kg/day) for two weeks followed by 2 mg/kg/day as maintenance, with the ability to titrate the dose down (e.g., in 0.5 mg/kg/day increments) to adjust for blood pressure response on an individual basis.

Example 5

An extensive use study was conducted to evaluate the six-month safety of telmisartan oral solution administered orally to cats for the control of systemic hypertension in cats. In particular, cats receiving telmisartan and completing the study of Example 4 were utilized for this extensive use study. The primary variables for assessment in this extensive use study were adverse events and change from baseline in retinal photographs. In general, the study of this example was conducted to show additional supportive safety data for extended treatment of cats with telmisartan.

Domestic cats greater than one year of age that met the enrollment criteria for the study of Example 4 were eligible for enrollment in this extended-use study. Additionally, the cat's mean Systolic Blood Pressure (mSBP) had to be ≤180 mmHg at Visit 3 (Day 28±2) in the previous study of Example 4. A total of 107 cats met the enrollment criteria and were utilized for this study. No placebo group was used in this study.

Cats were identified as belonging to one or more of the same three subpopulations as in Example 4 (CKD and/or hyperthyroidism or idiopathic hypertension), where a cat could have been enrolled into the CKD and hyperthyroid populations if it had both diseases. The subpopulations of the cats in this study are set forth in Table 10 below:

TABLE 10

| Subpopulation allocation (4 populations) | |
|---|---|
| Subpopulation | Total N (%) |
| CKD | 63 (58.9%) |
| Idiopathic | 31 (29.0%) |
| CKD and Hyperthyroid | 10 (9.3%) |
| Hyperthyroid | 3 (2.8%) |
| Total Across Subpopulations | 107 |

As indicated in Table 10, the populations enrolled in this extended use study, the majority were enrolled into the CKD subpopulation (68.2%). The idiopathic subpopulation represented 29.0%, followed by the hyperthyroid subpopulation at 12.1%. The percentages do not total 100% because a majority of the hyperthyroid subpopulation cats were also included in the CKD subpopulation. When the hyperthyroid subpopulation is separated into an additional subpopulation (CKD and hyperthyroid), it represents 9.3% of the study population.

As in Example 4, the dosing regimen for each cat in this study was implemented using a dosing syringe demarcated in 0.1 mL increments and based upon the weight of the cat at each visit. Upon enrollment into this extended-use study, the majority of cats (90.7%) were receiving a maintenance dose of 2 mg/kg once daily (SID). The maintenance dose was down-titrated if the mSBP was below the target range of 120-160 mmHg at any visit. In those cases, the dose was reduced to 1 mg/kg and further reduced to 0.5 mg/kg SID if mSBP remained below the target range. Twenty-six of the 107 cats had doses down-titrated during this extended-use study.

In particular, cats enrolled in this extended study were initially administered a dose of telmisartan of 2 mg/kg SID. If a cat's mSBP dropped below the targeted range (<120 mmHg), the dose was decreased or down titrated within the range of 0.5-2 mg/kg SID. The dose was chosen based on the mSBP values in Table 11 below:

TABLE 11

| | Dosing | | |
|---|---|---|---|
| | | - Treatment - | |
| Treatment type | SBP observed (mm Hg) | Dose of active ingredient (rate) | Dosage (volume) |
| Telmisartan Oral Solution (IVP) | >180 | Rescue | Rescue |
| | 180-120 | 2 mg/kg SID | 0.5 mL/kg SID |
| | <120 | 1 mg/kg SID* | 0.25 mL/kg SID* |

*After a cat received 1 mg/kg SID dosing, additional dose reduction was allowed to a minimum of 0.5 mg/kg SID or 0.125 mL/kg SID if mSBP was <120 mmHg. If at any visit the dose was the same as a dose the animal had been on previously AND that dose was known for that animal to have been too high or too low (causes the animal to be outside the targeted range of 120-160 mmHg), the Investigator may have chosen an alternate dose (within the allowed range of 0.5-2.0 mg/kg SID) in order to maintain the animal in the targeted range (120-160 mmHg).

Thus, the daily telmisartan dose for each cat was titrated, if necessary, at each visit according to the mSBP criteria set forth in Table 11. If, at any visit, the dose was the same as a dose the cat had previously received and that dose was known to be too high or too low for the cat (i.e., it caused the mSBP of the animal to be outside the targeted range of 120-160 mmHg), an alternate dose (within the allowed range of 0.5-2.0 mg/kg SID) was optionally chosen to maintain the animal in the targeted range (120-160 mmHg). An example of how one cat in this study had its daily dosage modified by being titrated down and up (based upon its measured mSBP value at each visit) is depicted in Table 12 below:

TABLE 12

| Dosing of Cat 329-454 | | |
|---|---|---|
| Study Visit | Mean SBP (mmHg) | Telmisartan daily dose (mg/kg) |
| Visit 1 (Week 0) | 160.0 | 3.0 (1.5 BID) |
| Visit 2 (Week 2) | 108.3 | 1.0 SID |
| Visit 3 (Week 4) | 116.0 | 0.5 SID |
| Visit 4 (Week 8) | 157.7 | 2.0 SID |
| Visit 5 (Week 14) | 100.0 | 1.0 SID |
| Visit 6 (Week 20) | 125.3 | 2.0 SID |
| Visit 7 (Week 26) | 126.0 | End of study |

Only 8 cats were removed from the study due to mSBP >180 mmHg, and were considered rescue cases. In summary, rescue cases accounted for 7.5% (8/107) of all end of study outcomes. This indicates that in 90.7% of cases (97/107), SBP was maintained within the target range (120-180 mmHg). Two cats (1.9% of the cases) were rescued due to hypotension.

Changes in mSBP and retinal photographs were assessed at Weeks 4, 14, and 26 (Days 28 ±2, 98 ±7, and 182 ±7, respectively) to monitor blood pressure control and to determine possible hypertension-related Target Organ Damage (TOD). Blood and urine values were documented at Weeks 4, 14, and 26 to support safety of telmisartan. At Weeks 8 (Day 56±7), Week 20 (Day 140±7), and at unscheduled visits, blood and urine samples were collected at the discretion of the Investigator. All parameters were evaluated by the Investigator for clinical significance. The parameters were then compared to baseline, and changes were summarized by treatment group as well as by subpopulation, if appropriate.

The data for group mean for blood pressure measurements and mean change in mSBP at Weeks 4, 8, 14, 20 and 26 are provided in the following Tables 13 and 14, respectively:

TABLE 13

Group mSBP by visit

| Visit | Mean (mmHg) | Median (mmHg) | Standard Error (mmHg) | Minimum mSBP (mmHg) | Maximum mSBP (mmHg) |
|---|---|---|---|---|---|
| Baseline (n = 107) | 176 | 175 | 1.1 | 160 | 200 |
| Week 4 (n = 107) | 148 | 149 | 1.8 | 95 | 179 |
| Week 8 (n = 102) | 148 | 148 | 2.0 | 105 | 195 |
| Week 14 (n = 92) | 142 | 144 | 2.1 | 77 | 207 |
| Week 20 (n = 81) | 145 | 148 | 2.0 | 89 | 184 |
| Week 26 (n = 73) | 150 | 147 | 2.2 | 104 | 207 |

TABLE 14

Mean change from baseline by visit

| Visit | Mean mSBP Change (ΔmmHg) | Median mSBP Change (ΔmmHg) | Standard Error (mmHg) | Minimum mSBP Change (ΔmmHg) | Maximum mSBP Change (ΔmmHg) |
|---|---|---|---|---|---|
| Week 4 (n = 107) | −29 | −26 | 1.9 | −76 | 14 |
| Week 8 (n = 102) | −28 | −28 | 1.9 | −79 | 7 |
| Week 14 (n = 92) | −33 | −32 | 2.2 | −115 | 25 |
| Week 20 (n = 81) | −30 | −28 | 1.9 | −91 | 16 |
| Week 26 (n = 73) | −25 | −28 | 2.2 | −69 | 30 |

The mSBP measured for the cats in the study at each visit was stable: 148 mmHg (Weeks 4 and 8), 142 mmHg (Week 14), 145 mmHg (Week 20), and 150 mmHg (Week 26), compared to 176 mmHg at baseline. This provides an indication that telmisartan can control SBP in this population of cats over an extended period of time.

The majority of cats (90.7%) were enrolled into the study at a dose of 2.0 mg/kg SID. Eight cats (7.5%) were enrolled at a dose of 1.0 mg/kg SID, and two cats (1.9%) were enrolled at a dose of 0.5 mg/kg SID. Throughout the study period, most cats (86.7%-88.8%) were maintained at a dose of 2.0 mg/kg. The remaining cats were down-titrated to either 1.0 mg/kg or 0.5 mg/kg. At the end of the study, most cats (87.7%) were receiving the 2.0 mg/kg dose. Table 15 provides the data for dose level of the cats at each visit:

TABLE 15

Dose level at each visit

| | Dose Level (SID) | | | | | |
|---|---|---|---|---|---|---|
| | 0.5 mg/kg | | 1.0 mg/kg | | 2.0 mg/kg | |
| Visit | N | % | N | % | N | % |
| Week 4 (N = 107) | 2 | 1.9% | 8 | 7.5% | 97 | 90.7% |
| Week 8 (N = 98) | 2 | 2.0% | 9 | 9.2% | 87 | 88.8% |
| Week 14 (N = 90) | 3 | 3.3% | 9 | 10.0% | 78 | 86.7% |
| Week 20 (N = 80) | 5 | 6.3% | 4 | 5.0% | 71 | 88.8% |
| Week 26 (N = 73) | 4 | 5.5% | 5 | 6.8% | 64 | 87.7% |

The specific case identified cats (a total of 26 cats) that were assigned a lower dose during the study due to having a SBP below 120 mmHg, is set forth in Table 16 below:

TABLE 16

Cases down titrated at each visit by new dose

| Visit | Cases (N) | Cases (IDs) |
|---|---|---|
| 1 mg/kg SID | | |
| Week 4 | 8 | 298-556, 308-474, 308-591, 317-405, 318-597, 325-560, 330-404, 330-509 |
| Week 8 | 7 | 263-505, 265-836, 322-490, 323-533, 325-661, 326-583, 331-1113 |
| Week 14 | 8 | 263-579, 264-404, 303-423, 305-409, 308-474, 308-754, 329-454, 329-535 |
| Week 20 | 3 | 269-434, 303-441, 334-465 |
| Unscheduled | 8 | 301-953, 318-794, 322-631, 323-514, 329-454, 329-599, 329-737, 331-888 |
| 0.5 mg/kg SID | | |
| Week 4 | 2 | 329-454, 358-406 |
| Week 8 | 2 | 298-556, 323-514 |
| Week 14 | 3 | 265-836, 322-631, 323-533 |
| Week 20 | 2 | 305-409, 308-474 |
| Unscheduled | 1 | 263-579 |
| <0.5 mg/kg SID = Hypotensive Rescue[+] | | |
| Week 8 | 0 | NA |
| Week 14 | 0 | NA |
| Week 20 | 1 | 263-579 |
| Unscheduled | 1 | 323-533 |

[+]Both cats were considered rescued based on mSBP <120 mmHg at visit following down titration to 0.5 mg/kg SID. Neither cat had clinical signs associated with hypotension; however, they were still removed from the study due to erroneous termination prompt from Sponsor in EDC system.

The data in Table 16 indicates that 9 cats were assigned a lower dose at Week 8, 11 cats at Week 14, 5 cats at Week 20, and 9 cats at an unscheduled visit. Of these cats, seven were down-titrated twice within the study period, and two were down-titrated three times. Two cats (263-579 and 323-533) were removed from the study due to continued hypotension (mSBP <120 mmHg) following reduction to the lowest allowable dose.

Serious AEs (SAES) occurred in 24 cats (22.4%) and Non-serious AEs (NSAEs) occurred in 91 cats (85.0%) during the study. The most commonly reported SAEs were weight loss (8.4%), anemia and dehydration (6.5%), anorexia, vomiting (5.6%), and lethargy, and the most common NSAEs were weight loss, vomiting, dehydration, and diarrhea. Overall, 11 SAEs were determined to be possibly attributable to telmisartan (10.3%). In general, considering the geriatric age of the enrolled population (mean of 14.1 years) and the cats targeted for recruitment (hypertensive cats with CKD and/or hyperthyroidism or idiopathic hypertension), the overall incidence of SAEs was as expected. The most common NSAEs (vomiting, diarrhea, and weight loss)

are common findings in geriatric cat studies and are expected in cats given oral medication. The AE assessment also involved clinical evaluation of developing or worsening of hypertension-related TOD. The results of this study showed that SAEs for TOD considered possibly related to telmisartan were substantially less prevalent than the values proposed in literature as typical.

For the assessment of change in retinal photographs, a majority of cats remained the same. Further, at all subsequent visits, 6.9% to 7.4% improved when compared to baseline. This indicates that telmisartan does not cause retinal deterioration and may promote improvement by decreasing the deleterious effects of hypertension on the retina.

IRIS staging and sub-staging were determined for all cats enrolled into the CKD and CKD and hyperthyroid subpopulations and having laboratory values at baseline. During the study period, a majority of cats remained the same regarding IRIS staging and proteinuria sub-staging. Furthermore, it is important to note that 83.0% to 98.1% of cats were scored as "better", and zero cats were scored as "worse" in the blood pressure sub-staging.

Figure 2:
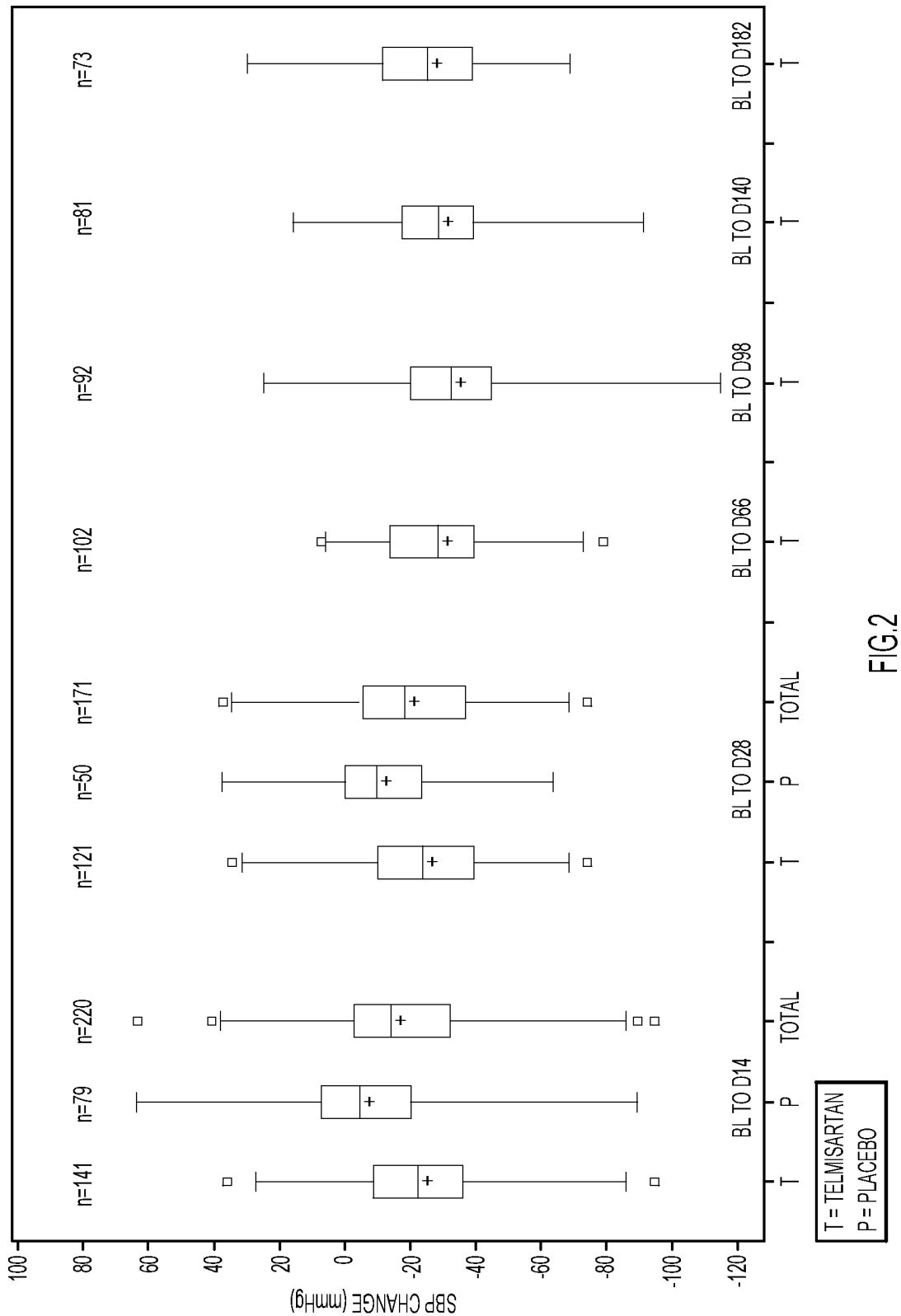
FIG. 2 is a plot of change in systolic blood pressure from baseline values for telmisartan and placebo groups for the studies of Examples 4 and 5.

The data plotted in FIG. 2 shows the SBP change from baseline at the start of each study for each of Examples 4 and 5 (where mean baseline was about 176 mmHg and mean baseline for placebo was about 175 mmHg). As is evident from the plotted data, the SBP change from baseline (with a reduction in SBP) was greater for the telmisartan group in relation to the placebo group at each of Day 14 and Day 28. In addition, the mean change in SBP for the telmisartan group was greater than 20 mmHg for each visit.

In conclusion, under clinical conditions, data from this study provide substantial evidence of the safety and effectiveness of telmisartan oral solution to control hypertension in cats at a dose of 2 mg/kg/day with the ability to titrate the dose to adjust for blood pressure response on an individual basis. This conclusion is based on the assessment of change in mSBP, adverse events (AEs), change in retinal photographs, and IRIS staging and sub-staging.

Example 6

A European study was conducted to investigate the efficacy and safety of telmisartan oral solution for the treatment of systemic hypertension in cats. The first part or phase of the study (Day 1 to Day 28) occurred over a 28-day placebo-controlled, double-blinded treatment period (efficacy phase of the study). In a second part or phase of the study (Day 29 to Day 120), the effect and safety of telmisartan on mean Systolic Blood Pressure (mSBP) control over an extended treatment period of an additional 92 days was also evaluated (extended use phase of the study). The mSBP was defined as the arithmetic mean of 3 blood pressure measurements at each study visit. Baseline SBP was defined as the arithmetic mean of the mSBP at Screening Visit Day -14 to -2 and Screening Visit Day -1.

Figure 3:
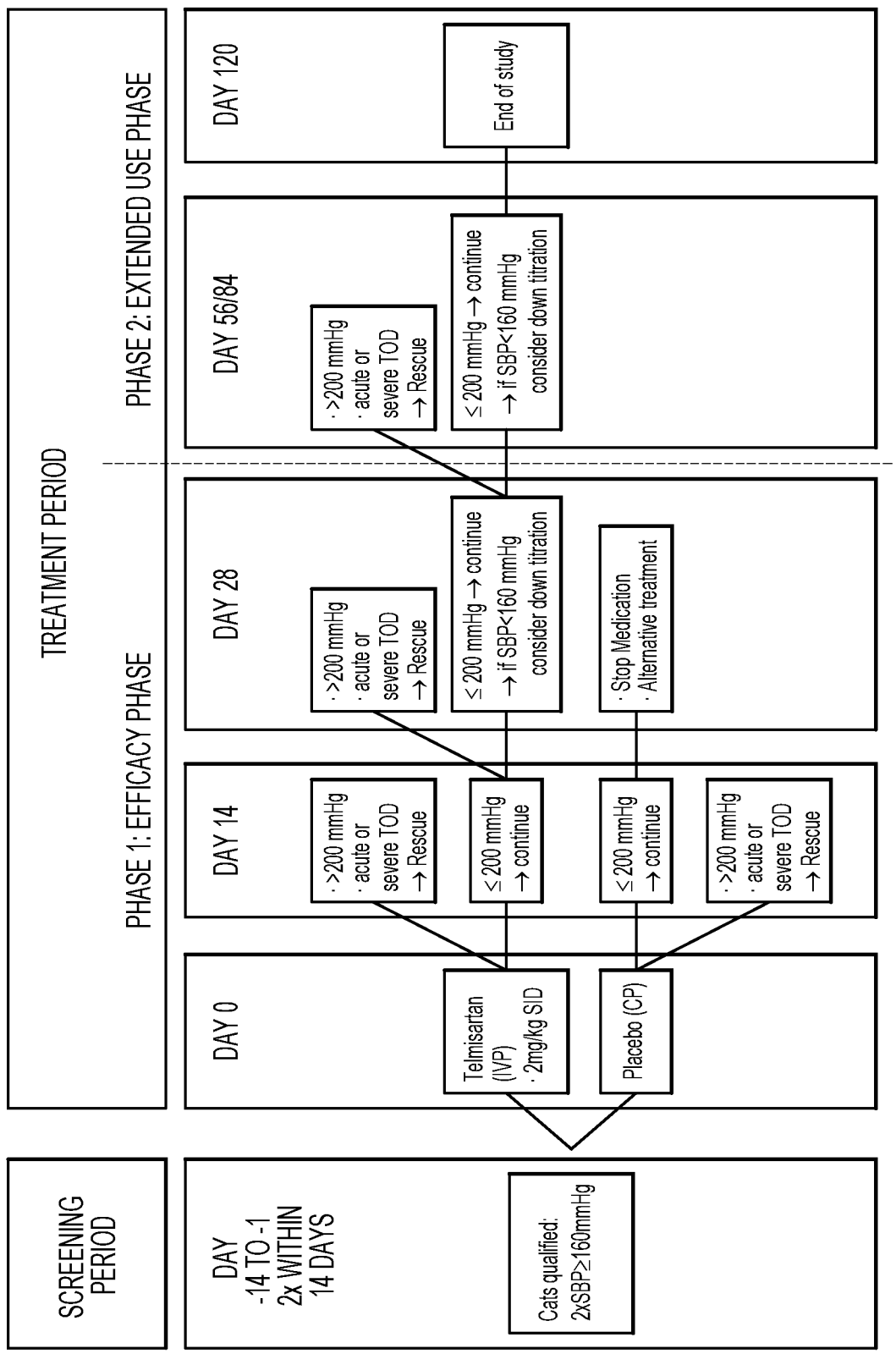
FIG. 3 depicts an overview of the study design for Example 6.

The target population for this study was domestic client-owned cats with moderate to severe systemic hypertension (cats having a mSBP of at least about 160 mmHg). A total of 285 client-owned cats from 51 study sites (24 in Germany, 9 in France, 11 in the United Kingdom, 4 in the Netherlands and 3 in Switzerland) were randomized for treatment with either telmisartan (189 cats, starting dose of 2.0 mg/kg once daily, which could be reduced from Day 28 onwards during the second [extended use] phase) or placebo (96 cats, 0.0 mg/kg once daily) in a 2:1 ratio. A schematic overview of the study and the two phases of treatment is depicted in FIG. 3. There was a similar pre-treatment mSBP observed for both treatment groups (about 177-179 mmHg).

Cats diagnosed with moderate to severe systemic hypertension in compliance with the "ACVIM consensus statement: Guidelines for the Identification, Evaluation, and Management of Systemic Hypertension in Dogs and Cats" (Brown et al. Guidelines for the identification, evaluation, and management of systemic hypertension in dogs and cats. ACVIM Consensus Statement. *J Vet Intern Med* 2007; 21: 542-558) at two separate Screening Visits within 14 days of the start of treatment were eligible for the study. The etiology of the hypertension was classified as due to chronic kidney disease (CKD), due to hyperthyroidism, due to both CKD and hyperthyroidism or as idiopathic hypertension. Cats were not allowed any substances which are known to affect blood pressure from 14 days prior to the start of treatment. Cats were excluded if their mSBP was in a malignant range (>200 mmHg) at Screening Visits, or if they had highly variable blood pressure measurements (differences over 3 consecutive measurements of >20%). Further exclusion criteria included uncontrolled hyperthyroidism (Total T4>60 nmol/L), acute or severe TOD, suspected or confirmed concomitant disease influencing blood pressure and/or likely to interfere with the study outcome, azotemia (due to acute or decompensated renal disease, pre- or post-renal factors or presenting a risk of non-completion of the study or hospitalization), or pregnant/lactating queens and cats intended for breeding.

Oral administration of the telmisartan solution (and placebo) was the route of delivery used in this study. During the development of telmisartan, studies with therapeutic doses of 1.0, 1.5, 2.0 and 3.0 mg/kg per day were initially conducted. The starting dose for the first phase of this study was set at 2.0 mg/kg per day of telmisartan orally. A 5 mL dosing syringe (demarcated in 0.25 mL increments) was used for the first phase and a 2 mL dosing syringe (demarcated in 0.1 mL increments, to achieve down titrations as necessary) to perform dosing either directly into the mouth of the cat or with a very small amount of food.

For the first (efficacy) phase of the study, all recruited cats were examined on two visits at Day 14 and Day 28. Examinations included measurement of mSBP, a complete physical examination, fundoscopic examination, an assessment of quality of life, and abbreviated clinical pathology (hematology and biochemistry). On Day 28, unmasking was performed and only cats assigned to telmisartan were allowed to continue forward for the second (extended use) phase of the study. These cats were further examined, as above, for visits at Days 56, 84 and 120. During the second (extended) phase of the study, it was possible to decrease or down titrate the dose for certain cats as described herein. In particular, it was possible (in this second phase of the study) to down titrate the dosage of telmisartan in cats with SBP measurement <160 mmHg in 0.5 mg/kg decrements or amounts (e.g., decreasing in a stepped manner from 2 mg/kg→1.5 mg/kg 4 1 mg/kg→0.5 mg/kg, SID) to the lowest possible dose of 0.5 mg/kg once a day upon the discretion of the Investigator.

At the outset of the study, the population of cats being administered telmisartan or placebo consisted of 189 cats in the telmisartan group and 96 cats in the placebo group. Certain cats were screened from the study at the conclusion due to various reasons (e.g., having a mSBP greater than 200, having certain severe TODs, certain cats did not complete the study, etc.). The safety of both phases of treatment was evaluated after the end of the study in utilizing a screened population consisting of 174 cats in the telmisartan group and 88 cats in the placebo group. The results of the study confirmed superiority of telmisartan over placebo after 14 days of treatment, and further demonstrated a clinically relevant decrease in mSBP (equal to or greater than 20 mmHg) after 28 days of treatment.

The treatment groups were homogenous with regard to breed, gender, age, body weight, baseline SBP, medical history and classification of hypertension. The data in relation to the number of cats in each hypertension classification per group (telmisartan and placebo) is set forth in Table 17 below:

TABLE 17

Classification of hypertension in each group

|  | Telmisartan (n = 189) | Placebo (n = 96) | Total (n = 285) |
|---|---|---|---|
| Baseline mSBP (mmHg) (±SD) | 179.3 (±9.9) | 177.4 (± 9.9) |  |
| Classification of hypertension [N (%)] | | | |
| Hypertension associated with CKD | 57 (30.2) | 30 (31.3) | 87 (30.5) |
| Hypertension associated with CKD and controlled hyperthyroidism | 9 (4.8) | 5 (5.2) | 14 (4.9) |
| Hypertension associated with controlled hyperthyroidism | 14 (7.4) | 7 (7.3) | 21 (7.4) |
| Idiopathic hypertension | 109 (57.7) | 54 (56.3) | 163 (57.2) |

A wide range of concomitant medications were administered during the study, and there were no clinically relevant changes in a physical or clinical pathology parameter observed in telmisartan-treated cats following 120 days of treatment. Although a similar appetite was observed in both treatment groups, more cats in the placebo group had a normal appetite on Day 28 than in the telmisartan treated group. However, the proportion of cats with increased appetite rose in the telmisartan group and decreased in the placebo group between day −1 and 28 (11% of the telmisartan treated cats had an increased appetite in comparison to 5.9% of the placebo treated cats). Overall, a total of 271 adverse events were recorded in 149 cats across both treatment groups and both treatment phases. During the efficacy phase, in the telmisartan group, a total of 115 adverse events were coded for 58 cats (29.9%), and in the placebo group, a total of 36 adverse events were coded for 29 cats (29%). Some differences were observed between the groups in the following categories: Renal and Urinary disorders, Eye disorders, Systemic disorders and Respiratory Tract disorders. The difference in the above mentioned disorders was related to various non-frequent medical conditions, which are typical for the included feline population except for Respiratory Tract disorders. The difference between the two groups regarding the Respiratory Tract disorders was due to numerous single incidental disorders related to both upper and lower respiratory tract. Observations considered by the Investigator to be most likely due to the treatment were gastrointestinal signs. During the second (extended use) phase, 62 cats (32.0%) had at least one adverse event. The diagnosis of TOD was very low in both treatment groups.

The data with regard to change in SBP for both the telmisartan and placebo groups in the first (efficacy) phase of the study (at Day 14 and Day 28) is set forth in Table 18 below (a visual representation of this data is also plotted in FIG. 5):

TABLE 18

Mean SBP changes during the first (efficacy) phase

| Parameter | Telmisartan | Placebo | Comparison | Endpoint successfully achieved |
|---|---|---|---|---|
| mSBP change (ΔmmHg) on Day 14 (95% Confidence Intervals) | n = 174 −19.219 (−22.52, −15.92) | n = 88 −9.045 (−12.80, −5.30) | p value of t-test < 0.0001 | Yes |
| mSBP change (ΔmmHg on Day 28 (95% Confidence Intervals) | n = 165 −24.629 (−28.14, −21.11) | n = 87 −11.44 (−14.95, −7.94) | Clinical relevance defined as mean systolic blood pressure change > 20 mmHg | Yes |

The mean differences of SBP changes on Day 14 in comparison to the baseline were −19.219 mmHg for the telmisartan group and −9.045 mmHg for the placebo group. The two-sided unequal variances t-test demonstrated superiority of telmisartan versus placebo by a p-value <0.0001. The mean difference between baseline SBP and SBP on Study Visit Day 28 was −24.629 mmHg for the telmisartan group. This value exceeded the minimum threshold of 20 mmHg which is required to demonstrate clinical relevance of the treatment effect, thus demonstrating the efficacy of telmisartan in comparison to placebo in the treatment of hypertension in cats.

The data with regard to change in SBP for the telmisartan group in the second (extended use) phase of the study (at Day 56, Day 84 and Day 120) is set forth in Table 19 below:

TABLE 19 mSBP changes during the second (extended use) phase

| Parameter | Telmisartan |
|---|---|
| Mean Systolic Blood Pressure change on Day 56 compared to baseline SBP (ΔmmHg): n = 152 cats (95% Confidence Intervals) | −26.94 (−30.79, −23.08) |
| Mean Systolic Blood Pressure change on Day 84 compared to baseline SBP (ΔmmHg): n = 148 cats (95% Confidence Intervals) | −26.50 (−30.60, −22.40) |
| Mean Systolic Blood Pressure change on Day 120 compared to baseline SBP (ΔmmHg): n = 144 cats (95% Confidence Intervals) | −27.62 (−32.05, −23.19) |

The data presented in Table 20 shows the mean SBP reduction over the different intervals/time periods of the study for cats in both the telmisartan group and the placebo group divided into two categories: baseline mSBP being between 160-179 mmHg and baseline mSBP being between 180-200 mmHg:

TABLE 20 mSBP changes at

| | SABP at baseline: | | | |
|---|---|---|---|---|
| | Between 160-179 mmHg | | between 180-200 mmHg | |
| | Telmisartan Baseline mSABP: 171.9 mmHg (n = 98) | Placebo Baseline mSABP: 170.9 mmHg (n = 56) | Telmisartan Baseline mSABP: 188.4 mmHg (n = 76) | Placebo Baseline mSABP: 188.5 mmHg (n = 32) |
| Visit | Mean SABP reduction (ΔmmHg) compared to baseline at respective visit (n = number of cats) | | | |
| Day 14 | −16.7 (n = 98) | −8.8 (n = 56) | −22.3 (n = 76) | −9.5 (n = 32) |
| Day 28 | −22.9 (n = 94) | −11.9 (n = 55) | −26.6 (n = 71) | −10.9 (n = 32) |
| Day 56 | −24.7 (n = 87) | NA | −29.6 (n = 65) | NA |
| Day 84 | −23.2 (n = 85) | NA | −30.7 (n = 63) | NA |
| Day 120 | −23.5 (n = 81) | NA | −32.9 (n = 63) | NA |

The data in Table 21 below summarizes a comparison in number of cats within each group in which the mSBP value was maintained below 160 mmHg:

TABLE 21

Frequency of cats with mSBP <160 mmHg

| Study Visit Day | Telmisartan | Placebo |
|---|---|---|
| | N (%) with Systolic Blood Pressure < 160 mmHg | |
| Pre-Treatment | 0 (0) | 0 (0) |
| Visit Day 14 | 81 (46.6) | 27 (30.7) |
| Visit day 28 | 101 (62.0) | 34 (40.0) |
| Visit Day 56 | 105 (70.9) | Not conducted |
| Visit Day 84 | 97 (67.8) | Not conducted |
| Visit Day 120 | 98 (73.1) | Not conducted |

The number of cats at each dosage amount at each visit day is set forth in Table 22 below:

TABLE 22

Overview of Telmisartan dose

| Study Visit Day | Mean Dose (mg/kg) (95% Confidence intervals) | Actual Dose (mg/kg) | Number of Cats receiving dose |
|---|---|---|---|
| Day 0 (n = 174) | 2.0 (NA) | 2.0 | 174 |
| Visit Day 14 (n = 174) | 2.0 (NA) | 2.0 | 174 |
| Visit day 28 (n = 163) | 1.95 (1.93-1.98) | 2.0 | 148 |
| | | 1.5 | 15 |
| Visit Day 56 (n = 148) | 1.89 (1.84-1.93) | 2.0 | 124 |
| | | 1.5 | 15 |
| | | 1.0 | 9 |
| Visit Day 84 (n = 143) | 1.84 (1.78-1.90) | 2.0 | 112 |
| | | 1.5 | 20 |
| | | 1.0 | 7 |
| | | 0.5 | 4 |

Figure 4:
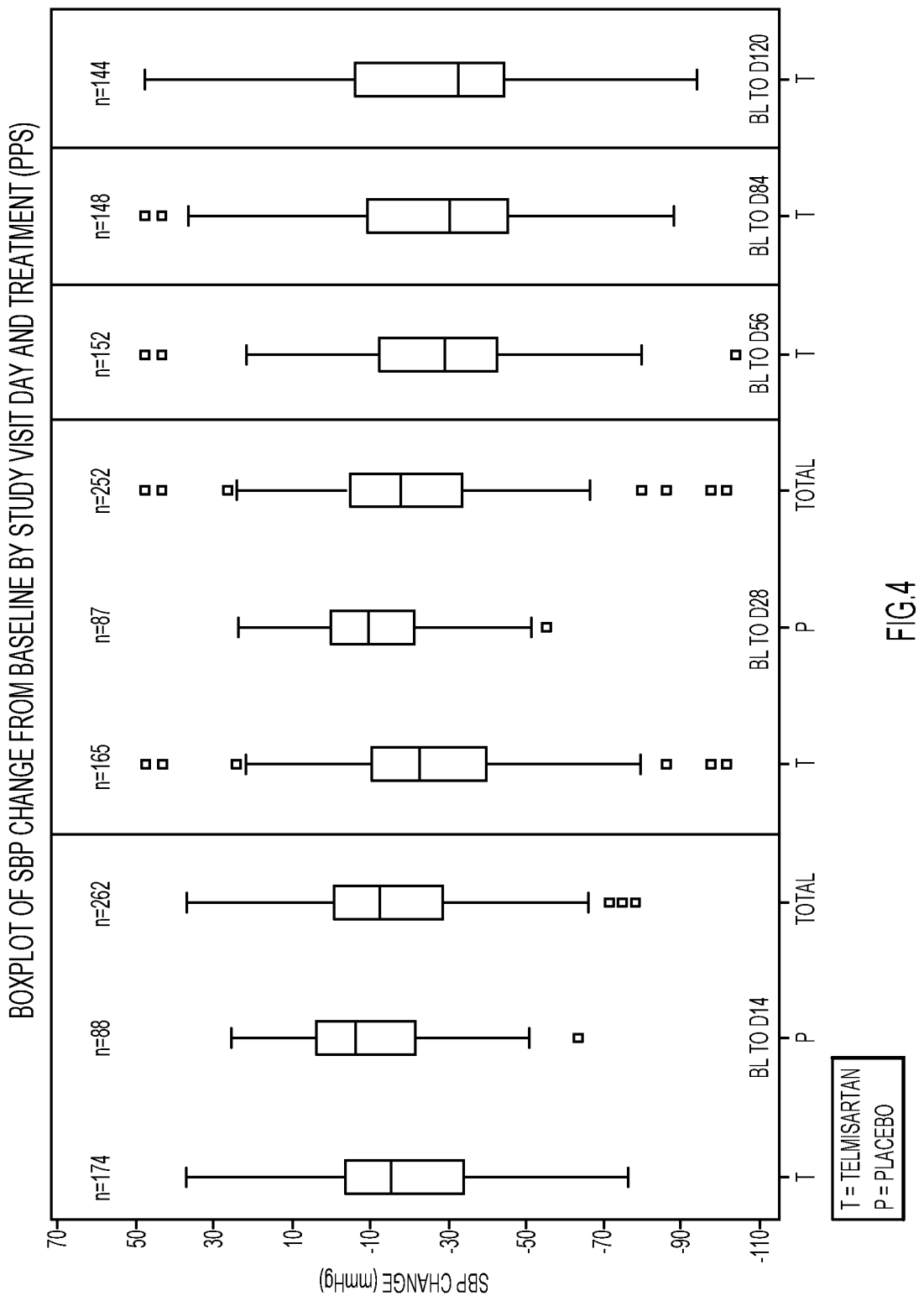
FIG. 4 is a box plot of change in systolic blood pressure from baseline values for telmisartan and placebo groups for the study of Example 6.
Figure 5:
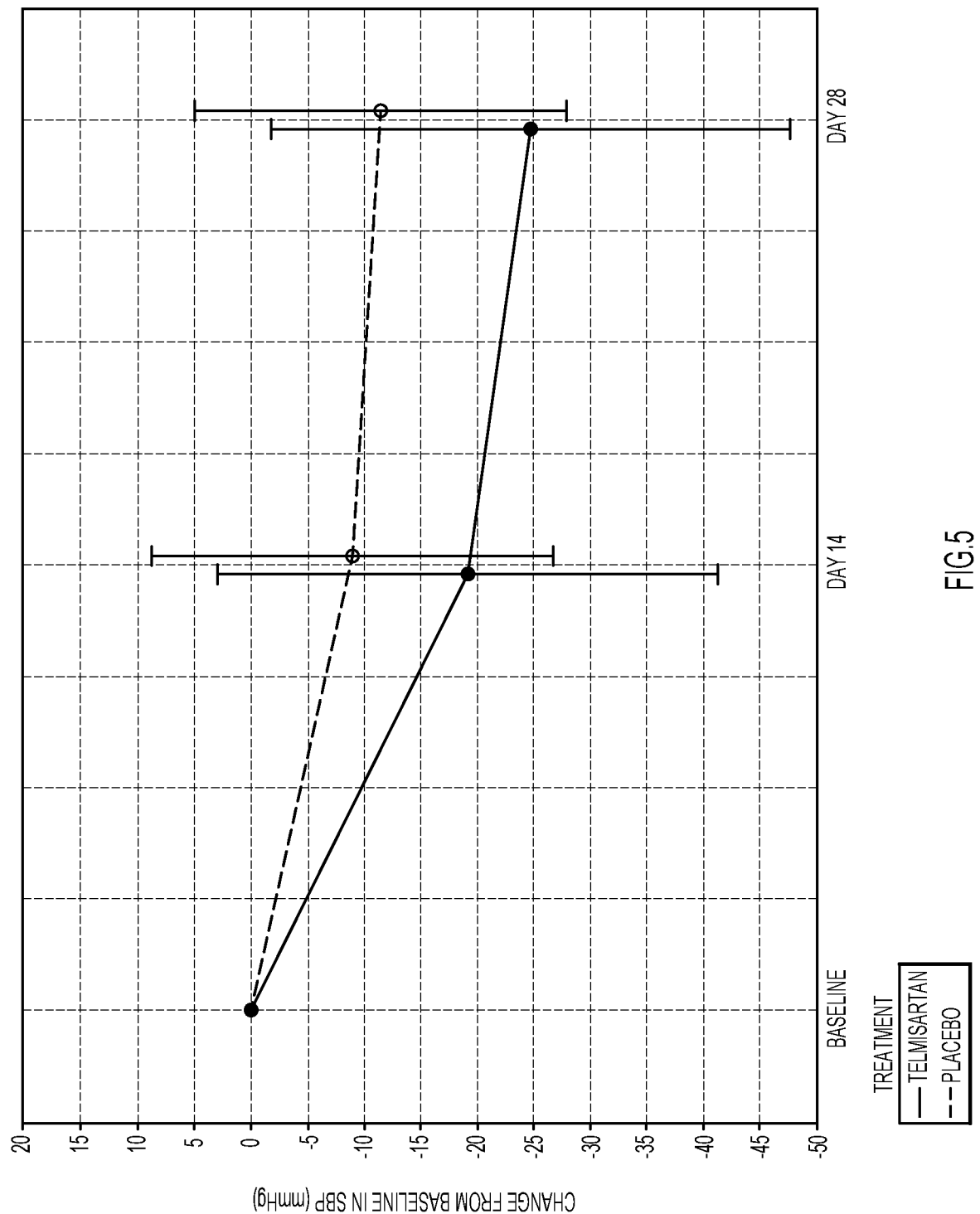
FIG. 5 is a plot of change in systolic blood pressure from baseline values for telmisartan and placebo groups at day 14 and day 28 for the study of Example 6.

The data plotted in FIGS. 4 and 5 show the SBP change from baseline (at start of the study for each of the first and second phases of this study). As is evident from the plotted data, the SBP change from baseline (with a reduction in SBP) was greater for the telmisartan group in relation to the placebo group in the first phase (Day 14 and Day 28). In addition, the mean change in SBP for the telmisartan group was greater than 20 mmHg for each of the visit days.

The second (extended use) phase indicates that treatment with telmisartan resulted in a sustained clinically relevant reduction in mSBP of greater than 20 mmHg for the whole study duration of 120 days. The SBP was restored to normal or levels considered to be only mild or minimal risk (<160 mmHg) in 62.0% of telmisartan-treated cats and it was possible to down-titrate the dose to <2 mg/kg in 21.7% of telmisartan treated cats.

During this study, a number of other physical parameters (in addition to measured SBP) for the cats were monitored (e.g., mean body weight, mean heart rate, respiratory rate, and rectal temperature). There was no clinically significant change observed in any of these parameters following 120 days treatment with telmisartan.

In conclusion, this study reveals that, in cats diagnosed with systemic hypertension, treatment with 2 mg/kg telmisartan oral solution was superior to placebo in reducing mSBP by a clinically relevant magnitude within the 28 days efficacy phase. A further 92 days of treatment with telmisartan oral solution was safe and maintained a clinically relevant reduction in mSBP.

What is claimed:

1. A kit in parts comprising:
a container containing a pharmaceutical composition in a liquid formulation comprising an angiotensin II receptor 1 (AT-1) antagonist (sartan) and one or more pharmaceutically acceptable diluents and/or carriers, the amount of sartan being within the liquid formulation in an amount that is therapeutically effective for the prophylaxis or treatment of hypertension in a cat in need of such treatment; and
a syringe comprising a barrel and including a plurality of volumetric graduation marks imprinted thereon in 0.10 mL increments or less.

2. The kit in parts of claim 1, wherein the plurality of volumetric graduation marks imprinted on the barrel include marks increments extending from 0 mL to 2.0 mL.

3. The kit in parts of claim 1, wherein the liquid formulation within the container includes telmisartan.

4. The kit in parts of claim 3, wherein the liquid formulation within the container includes telmisartan in an amount of 10 mg/mL.

5. The kit in parts of claim 1, further comprising a second container containing a pharmaceutical composition other than an angiotensin II receptor 1 (AT-1) antagonist (sartan).

6. The kit in parts of claim 5, wherein the pharmaceutical composition of the second container is effective for the prophylaxis or treatment of a systemic disease in a cat in need of such treatment.

7. A kit in parts comprising:
a container containing a pharmaceutical composition in a liquid formulation comprising an angiotensin II receptor 1 (AT-1) antagonist (sartan) and one or more pharmaceutically acceptable diluents and/or carriers, the amount of sartan being within the liquid formulation in an amount that is therapeutically effective for the prophylaxis or treatment of hypertension in a cat in need of such treatment;
a syringe comprising a barrel and including a plurality of volumetric graduation marks imprinted thereon in 0.25 mL increments or less; and
an adaptor that connects with an open end of the container, the adaptor including an opening extending through the adaptor, wherein the adaptor opening is smaller in dimension than the container open end, the adaptor opening is at least partially defined by walls extending inward from an end of the adaptor, and the syringe barrel includes an open end having a frustoconical shaped portion that corresponds with a geometry of the adaptor opening defined by the inward extending walls to facilitate a frictional fit between the barrel open end and the adaptor when the barrel open end is inserted into the adaptor opening with full receipt of the frustoconical shaped portion of the barrel within the adaptor opening.

8. The kit in parts of claim 7, wherein the geometry of the adaptor opening prevents another syringe that has a geometry different from the geometry of the syringe barrel open end from connecting with the adaptor.

* * * * *